US009605048B2

(12) United States Patent
Blot-Chabaud et al.

(10) Patent No.: US 9,605,048 B2
(45) Date of Patent: Mar. 28, 2017

(54) HUMAN SOLUBLE CD146, PREPARATION AND USES THEREOF

(75) Inventors: Marcel Blot-Chabaud, Fuveau (FR); Karim Harhouri, Marseilles (FR); Nathalie Bardin, Marseilles (FR); Benjamin Guillet, Aix en Provence (FR); Françoise Dignat-George, Marseilles (FR)

(73) Assignees: UNIVERSITE D'AIX-MARSEILLE, Marseilles (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 304 days.

(21) Appl. No.: 13/146,758

(22) PCT Filed: Jan. 29, 2010

(86) PCT No.: PCT/EP2010/051080
§ 371 (c)(1),
(2), (4) Date: Jul. 28, 2011

(87) PCT Pub. No.: WO2010/086405
PCT Pub. Date: Aug. 5, 2010

(65) Prior Publication Data
US 2011/0286963 A1    Nov. 24, 2011

(30) Foreign Application Priority Data

Jan. 30, 2009    (EP) .................................... 09305093

(51) Int. Cl.
*A61K 38/00* (2006.01)
*C07K 1/107* (2006.01)
*C07K 14/705* (2006.01)

(52) U.S. Cl.
CPC ........ *C07K 14/70503* (2013.01); *A61K 38/00* (2013.01)

(58) Field of Classification Search
USPC ........................................... 514/3.9; 530/396
See application file for complete search history.

(56) References Cited

U.S. PATENT DOCUMENTS

| | | | |
|---|---|---|---|
| 6,133,231 A * | 10/2000 | Ferrara et al. | 514/7.6 |
| 6,824,995 B1 | 11/2004 | Wu | |
| 7,309,687 B1 * | 12/2007 | Brines et al. | 514/7.7 |
| 8,338,385 B2 * | 12/2012 | Kim et al. | 514/44 R |
| 2007/0231323 A1 * | 10/2007 | Phillips | 424/133.1 |
| 2008/0050730 A1 * | 2/2008 | Modiano et al. | 435/6 |

FOREIGN PATENT DOCUMENTS

WO    WO 02/079492    10/2002

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Kebir et al. CD146 short isoform increases the proangiogenic potential of endothelial progenitor cells in vitro and in vivo. Circ. Res. vol. 107:66-75; 2010 (published online May 6, 2010.).*
Pu et al. A persistent hindlimb ischemia model in rabbit. Journal Investigative Surgery, Abstract Jan.-Feb. 7(1) 49-60 (1994).*
Wu et al. METCAM/MUC18, a cell adhesion molecule, plays positive and negative roles in the progression of different cancers. Current Topics in Genetics Abstract vol. 4, pp. 79-93 (2010).*
Wu et al. METCAM promotes in vitro motility, invasiveness and colony formation, and in vivo tumorigenesis of human breast cancer cells. Cancer Research, vol. 70, No. 8, Supp. Suppl. 1. Abstract No. 481 (Apr. 15, 2010).*
Guezguez et al. Dual role of melanoma cell adhesion molecule (MCAM)/CD146 in lymphocyte endothelium interaction: MCAM/CD146 promotes rolling via microvilli induction in lymphoyctes and is an endothelial adhesion receptor. The Journal of Immunology vol. 179:6673-6685 (2007).*
Yan, X. et al. "A novel anti-CD146 monoclonal antibody, AA98, inhibits angiogenesis and tumor growth" *Blood*, Jul. 1, 2003, pp. 184-191, vol. 102, No. 1.
Lin, Y. et al. "A Novel Antibody AA98 $V_H/L$ Directed Against CD146 Efficiently Inhibits Angiogenesis" *AntiCancer Research*, Nov. 1, 2007, pp. 4219-4224, vol. 27.
Bardin, N. et al. "Soluble CD146, a novel endothelial marker, is increased in physiopathological settings linked to endothelial junctional alteration" *Thrombosis and Haemostasis*, Nov. 1, 2003, pp. 915-920, vol. 90, No. 5.
Bardin, N. et al. "Soluble CD164, a junctional endothelial adhesion molecule, is increased in vascular disorders" *Tissue Antigens*, Jan. 1, 2000, p. 63, vol. 55.
Bardin, N. et al. "CD146: biosynthesis and production of a soluble form in human cultured endothelial cells" *FEBS Letters*, Jan. 2, 1998, pp. 12-14, vol. 421.
Wu, G. et al. "Soluble METCAM/MUC18 blocks angiogenesis during the in vivo tumor formation of human prostate cancer LNCaP cells" #252, *Proceedings of the American Association for Cancer Research*, Apr. 2006, p. 59, vol. 47.
Written Opinion in International Application No. PCT/EP2010/051080, Apr. 22, 2010, pp. 1-7.

* cited by examiner

*Primary Examiner* — Elizabeth C Kemmerer
*Assistant Examiner* — Regina M Deberry
(74) *Attorney, Agent, or Firm* — Saliwanchik, Lloyd & Eisenschenk

(57) ABSTRACT

The present invention relates to compositions and methods for modulating angiogenesis in vivo, ex vivo or in vitro. More particularly, the invention relates to a soluble CD 146 protein usable in the context of human therapy, as well as to corresponding antibodies. Particular forms of CD 146, herein described, may be used to mobilize, in vivo or ex vivo, both mature and immature endothelial cells, as well as to increase their influence on angiogenesis. The invention also relates to compositions comprising such compounds, particularly pharmaceutical or diagnostic compositions, including kits and the like, as well as methods of therapy or diagnosis using said compounds, compositions and cells.

Figure 1A:
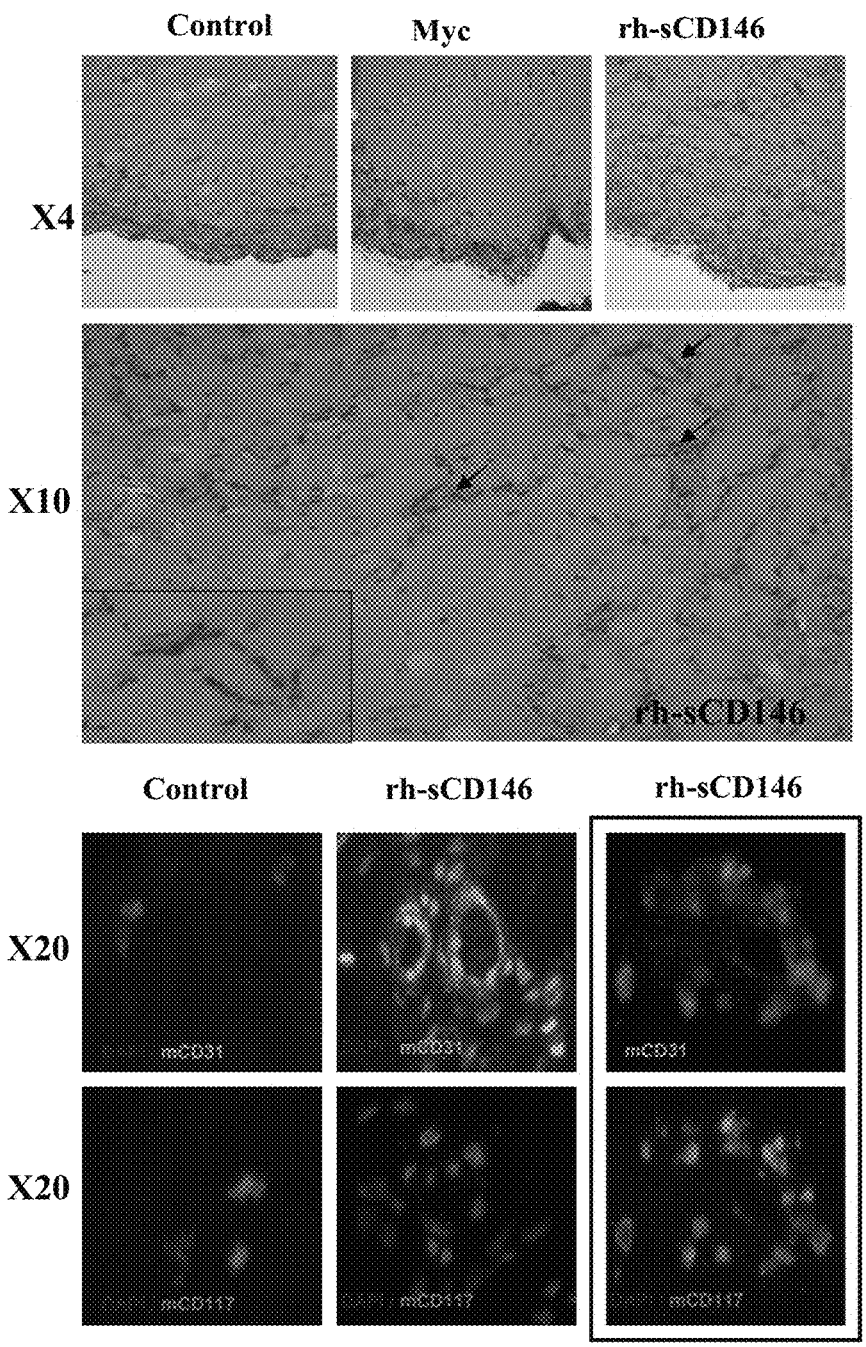

9 Claims, 17 Drawing Sheets
(7 of 17 Drawing Sheet(s) Filed in Color)

X40

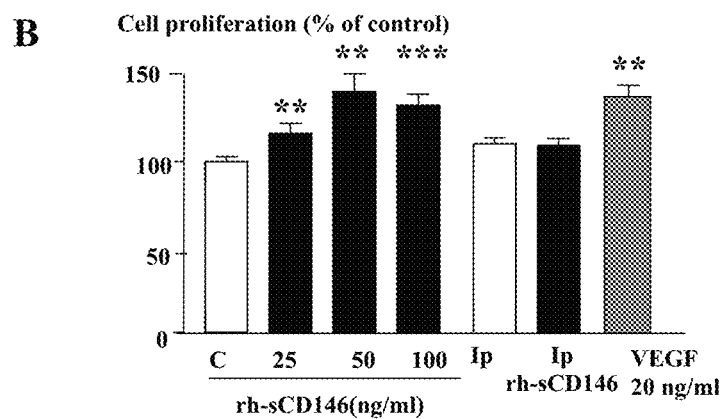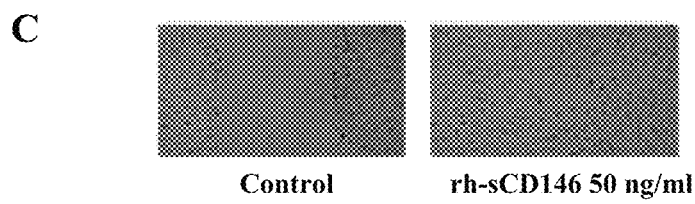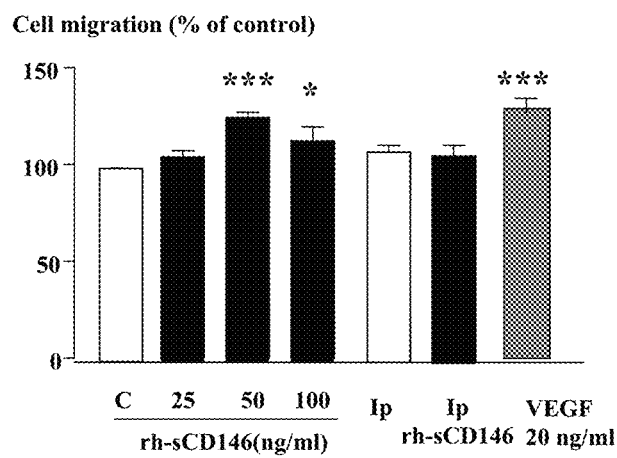
FIGURES 2B and 2C

|  | inflammation | fibrosis | necrosed fibers | angiogenesis | muscle aspect |
|---|---|---|---|---|---|
| Control | + | ++ | ++ | +/- | +/- |
| Myc 12 days | + | ++ | ++ | +/- | +/- |
| rh-sCD146 12days | +/- | - | +/- | ++ | +++ |

FIGURE 4C

SEQUENCE LISTING

<160> NUMBER OF SEQ ID NOS: 26

<210> SEQ ID NO 1
<211> LENGTH: 552
<212> TYPE: PRT
<213> ORGANISM: Homo sapiens
<220> FEATURE:

<221> NAME/KEY: MISC_FEATURE
<223> OTHER INFORMATION: Amino acid sequence of human soluble CD146
      protein (1)

<400> SEQUENCE: 1

```
Met Gly Leu Pro Arg Leu Val Cys Ala Phe Leu Leu Ala Ala Cys Cys
1               5                   10                  15
Cys Cys Pro Arg Val Ala Gly Val Pro Gly Glu Ala Glu Gln Pro Ala
                20                  25                  30
Pro Glu Leu Val Glu Val Glu Val Gly Ser Thr Ala Leu Leu Lys Cys
            35                  40                  45
Gly Leu Ser Gln Ser Gln Gly Asn Leu Ser His Val Asp Trp Phe Ser
    50                  55                  60
Val His Lys Glu Lys Arg Thr Leu Ile Phe Arg Val Arg Gln Gly Gln
65                  70                  75                  80
Gly Gln Ser Glu Pro Gly Glu Tyr Glu Gln Arg Leu Ser Leu Gln Asp
                85                  90                  95
Arg Gly Ala Thr Leu Ala Leu Thr Gln Val Thr Pro Gln Asp Glu Arg
            100                 105                 110
Ile Phe Leu Cys Gln Gly Lys Arg Pro Arg Ser Gln Glu Tyr Arg Ile
    115                 120                 125
Gln Leu Arg Val Tyr Lys Ala Pro Glu Glu Pro Asn Ile Gln Val Asn
130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Glu Lys Asn Arg Val His Ile Gln Ser
            180                 185                 190
Ser Gln Thr Val Glu Ser Ser Gly Leu Tyr Thr Leu Gln Ser Ile Leu
    195                 200                 205
Lys Ala Gln Leu Val Lys Glu Asp Lys Asp Ala Gln Phe Tyr Cys Glu
    210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
            260                 265                 270
Leu Ala Asp Gly Asn Pro Pro Pro His Phe Ser Ile Ser Lys Gln Asn
    275                 280                 285
Pro Ser Thr Arg Glu Ala Glu Glu Thr Thr Asn Asp Asn Gly Val
290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Leu Ser Glu Pro Gln
                325                 330                 335
Glu Leu Leu Val Asn Tyr Val Ser Asp Val Arg Val Ser Pro Ala Ala
            340                 345                 350
Pro Glu Arg Gln Glu Gly Ser Ser Leu Thr Leu Thr Cys Glu Ala Glu
    355                 360                 365
Ser Ser Gln Asp Leu Glu Phe Gln Trp Leu Arg Glu Glu Thr Asp Gln
    370                 375                 380
Val Leu Glu Arg Gly Pro Val Leu Gln Leu His Asp Leu Lys Arg Glu
```

```
                    385                 390                 395                 400
Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
                435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
                515                 520                 525

Thr Thr Gly Leu Ser Ser Thr Ala Ser Pro His Thr Arg Ala Asn
                530                 535                 540

Ser Thr Ser Thr Glu Arg Lys Leu
545                 550

<210> SEQ ID NO 2
<211> LENGTH: 553
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
      protein (2)

<400> SEQUENCE: 2

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
                35                  40                  45

Gly Leu Ser Gln Ser Gln Gly Asn Leu Ser His Val Asp Trp Phe Ser
            50                  55                  60

Val His Lys Glu Lys Arg Thr Leu Ile Phe Arg Val Arg Gln Gly Gln
65              70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
                115                 120                 125

Gln Leu Arg Val Tyr Lys Ala Pro Glu Glu Pro Asn Ile Gln Val Asn
            130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190
```

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
        210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro
545                 550

<210> SEQ ID NO 3
<211> LENGTH: 554
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
    protein (3)

<400> SEQUENCE: 3

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
                260                 265                 270

Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
```

```
                405                 410                 415
Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
            485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr
    515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu
545                 550

<210> SEQ ID NO 4
<211> LENGTH: 555
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
      protein (4)

<400> SEQUENCE: 4

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
            85                  90                  95

Arg Gly Ala Thr Leu Ala Leu Thr Gln Val Thr Pro Gln Asp Glu Arg
        100                 105                 110

Ile Phe Leu Cys Gln Gly Lys Arg Pro Arg Ser Gln Glu Tyr Arg Ile
    115                 120                 125

Gln Leu Arg Val Tyr Lys Ala Pro Glu Glu Pro Asn Ile Gln Val Asn
130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
            165                 170                 175

Asn Gly Arg Pro Leu Lys Glu Glu Lys Asn Arg Val His Ile Gln Ser
        180                 185                 190

Ser Gln Thr Val Glu Ser Ser Gly Leu Tyr Thr Leu Gln Ser Ile Leu
    195                 200                 205
```

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro
545                 550                 555

<210> SEQ ID NO 5
<211> LENGTH: 556
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
      protein (5)

<400> SEQUENCE: 5

-continued

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
            85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Pro Asn Ile Gln Val Asn
        130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
            325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
            405                 410                 415

Leu Asn Arg Thr Gln Leu Val Lys Leu Ala Ile Phe Gly Pro Pro Trp
```

```
                420               425               430
Met Ala Phe Lys Glu Arg Lys Val Trp Val Lys Glu Asn Met Val Leu
            435               440               445

Asn Leu Ser Cys Glu Ala Ser Gly His Pro Arg Pro Thr Ile Ser Trp
450                 455               460

Asn Val Asn Gly Thr Ala Ser Glu Gln Asp Gln Asp Pro Gln Arg Val
465                 470               475               480

Leu Ser Thr Leu Asn Val Leu Val Thr Pro Glu Leu Leu Glu Thr Gly
            485               490               495

Val Glu Cys Thr Ala Ser Asn Asp Leu Gly Lys Asn Thr Ser Ile Leu
            500               505               510

Phe Leu Glu Leu Val Asn Leu Thr Thr Leu Thr Pro Asp Ser Asn Thr
            515               520               525

Thr Thr Gly Leu Ser Thr Ser Thr Ala Ser Pro His Thr Arg Ala Asn
            530               535               540

Ser Thr Ser Thr Glu Arg Lys Leu Pro Glu Pro Glu
545                 550               555
```

<210> SEQ ID NO 6
<211> LENGTH: 557
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
      protein (6)

<400> SEQUENCE: 6

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220
```

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
            245                 250                 255

Glu Pro Val Gly Met Leu Lys Glu Gly Asp Arg Val Gly Ile Arg Cys
        260                 265                 270

Leu Ala Asp Gly Asn Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
            325                 330                 335

Glu Leu Leu Val Asn Tyr Val Ser Asp Val Arg Val Ser Pro Ala Ala
        340                 345                 350

Pro Glu Arg Gln Glu Gly Ser Ser Leu Thr Leu Thr Cys Glu Ala Glu
    355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
            405                 410                 415

Leu Asn Arg Thr Gln Leu Val Lys Leu Ala Ile Phe Gly Pro Pro Trp
        420                 425                 430

Met Ala Phe Lys Glu Arg Lys Val Trp Val Lys Glu Asn Met Val Leu
    435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
            485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr
    515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser
545                 550                 555

<210> SEQ ID NO 7
<211> LENGTH: 558
<212> TYPE: PRT
<213> ORGANISM: Homo sapiens
<220> FEATURE:
<221> NAME/KEY: MISC_FEATURE
<223> OTHER INFORMATION: Amino acid sequence of human soluble CD146
      protein (7)

<400> SEQUENCE: 7

Met Gly Leu Pro Arg Leu Val Cys Ala Phe Leu Leu Ala Ala Cys Cys
1               5                   10                  15

```
Cys Cys Pro Arg Val Ala Gly Val Pro Gly Glu Ala Glu Gln Pro Ala
             20                  25                  30
Pro Glu Leu Val Glu Val Glu Val Gly Ser Thr Ala Leu Leu Lys Cys
         35                  40                  45
Gly Leu Ser Gln Ser Gln Gly Asn Leu Ser His Val Asp Trp Phe Ser
 50                  55                  60
Val His Lys Glu Lys Arg Thr Leu Ile Phe Arg Val Arg Gln Gly Gln
 65                  70                  75                  80
Gly Gln Ser Glu Pro Gly Glu Tyr Glu Gln Arg Leu Ser Leu Gln Asp
                 85                  90                  95
Arg Gly Ala Thr Leu Ala Leu Thr Gln Val Thr Pro Gln Asp Glu Arg
                100                 105                 110
Ile Phe Leu Cys Gln Gly Lys Arg Pro Arg Ser Gln Glu Tyr Arg Ile
             115                 120                 125
Gln Leu Arg Val Tyr Lys Ala Pro Glu Glu Pro Asn Ile Gln Val Asn
         130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Glu Lys Asn Arg Val His Ile Gln Ser
                180                 185                 190
Ser Gln Thr Val Glu Ser Ser Gly Leu Tyr Thr Leu Gln Ser Ile Leu
            195                 200                 205
Lys Ala Gln Leu Val Lys Glu Asp Lys Asp Ala Gln Phe Tyr Cys Glu
210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
            260                 265                 270
Leu Ala Asp Gly Asn Pro Pro His Phe Ser Ile Ser Lys Gln Asn
         275                 280                 285
Pro Ser Thr Arg Glu Ala Glu Glu Thr Thr Asn Asp Asn Gly Val
         290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Leu Ser Glu Pro Gln
            325                 330                 335
Glu Leu Leu Val Asn Tyr Val Ser Asp Val Arg Val Ser Pro Ala Ala
                340                 345                 350
Pro Glu Arg Gln Glu Gly Ser Ser Leu Thr Leu Thr Cys Glu Ala Glu
        355                 360                 365
Ser Ser Gln Asp Leu Glu Phe Gln Trp Leu Arg Glu Glu Thr Asp Gln
    370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
                405                 410                 415
Leu Asn Arg Thr Gln Leu Val Lys Leu Ala Ile Phe Gly Pro Pro Trp
            420                 425                 430
Met Ala Phe Lys Glu Arg Lys Val Trp Val Lys Glu Asn Met Val Leu
```

```
            435                 440                 445
Asn Leu Ser Cys Glu Ala Ser Gly His Pro Arg Pro Thr Ile Ser Trp
450                 455                 460

Asn Val Asn Gly Thr Ala Ser Glu Gln Asp Gln Pro Gln Arg Val
465                 470                 475                 480

Leu Ser Thr Leu Asn Val Leu Val Thr Pro Glu Leu Leu Glu Thr Gly
                    485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
        530                 535                 540

Ser Thr Ser Thr Glu Arg Lys Leu Pro Glu Pro Glu Ser Arg
545                 550                 555
```

<210> SEQ ID NO 8
<211> LENGTH: 646
<212> TYPE: PRT
<213> ORGANISM: Homo sapiens
<220> FEATURE:
<221> NAME/KEY: MISC_FEATURE
<223> OTHER INFORMATION: Amino acid sequence of human long CD146 protein

<400> SEQUENCE: 8

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240
```

```
Val Thr Val Pro Val Phe Tyr Pro Thr Glu Lys Val Trp Leu Glu Val
            245                 250                 255

Glu Pro Val Gly Met Leu Lys Glu Gly Asp Arg Val Glu Ile Arg Cys
        260                 265                 270

Leu Ala Asp Gly Asn Pro Pro His Phe Ser Ile Ser Lys Gln Asn
        275                 280                 285

Pro Ser Thr Arg Glu Ala Glu Glu Thr Thr Asn Asp Asn Gly Val
        290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
        530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Thr Glu Leu
            595                 600                 605

Val Val Glu Val Lys Ser Asp Lys Leu Pro Glu Glu Met Gly Leu Leu
610                 615                 620

Gln Gly Ser Ser Gly Asp Lys Arg Ala Pro Gly Asp Gln Gly Glu Lys
625                 630                 635                 640

Tyr Ile Asp Leu Arg His
                645
```

-continued

```
<210> SEQ ID NO 9
<211> LENGTH: 604
<212> TYPE: PRT
<213> ORGANISM: Homo sapiens
<220> FEATURE:
<221> NAME/KEY: MISC_FEATURE
<223> OTHER INFORMATION: Amino acid sequence of human short CD146
      protein

<400> SEQUENCE: 9

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365
```

Ser Ser Gln Asp Leu Glu Phe Gln Trp Leu Arg Glu Thr Asp Gln
    370                 375                 380

Val Leu Glu Arg Gly Pro Val Leu Gln Leu His Asp Leu Lys Arg Glu
385                 390                 395                 400

Ala Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
                500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Met Glu Arg Asn Thr Ser Ile
    595                 600

<210> SEQ ID NO 10
<211> LENGTH: 1656
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146
      protein (1)

<400> SEQUENCE: 10
atggggcttc ccaggctggt ctgcgccttc ttgctcgccg cctgctgctg ctgtcctcgc       60
gtcgcgggtg tgcccggaga ggctgagcag cctgcgcctg agctggtgga ggtggaagtg      120
ggcagcacag cccttctgaa gtgcggcctc tcccagtccc aaggcaacct cagccatgtc      180
gactggtttt ctgtccacaa ggagaagcgg acgctcatct ccgtgtgcg ccagggccag       240 ggccagagcg aacctgggga gtacgagcag cggctcagcc tccaggacag aggggctact      300
ctggccctga ctcaagtcac cccccaagac gagcgcatct tcttgtgcca gggcaagcgc      360
cctcggtccc aggagtaccg catccagctc cgcgtctaca agctccggga ggagccaaac      420
atccaggtca cccccctggg catccctgtg aacagtaagg agcctgagga ggtcgctacc      480
tgtgtaggga ggaacgggta ccccattcct caagtcatct ggtacaagaa tggccggcct      540
ctgaaggagg agaagaaccg ggtccacatt cagtcgtccc agactgtgga gtcgagtggt      600
ttgtacacct tgcagagtat tctgaaggca cagctggtta agaagacaa agatgcccag       660

```
ttttactgtg agctcaacta ccggctgccc agtgggaacc acatgaagga gtccagggaa      720
gtcaccgtcc ctgttttcta cccgacagaa aaagtgtggc tggaagtgga gcccgtggga      780
atgctgaagg aaggggaccg cgtggaaatc aggtgtttgg ctgatggcaa ccctccacca      840
cacttcagca tcagcaagca gaaccccagc accaggagg cagaggaaga acaaccaac        900 gacaacgggg tcctggtgct ggagcctgcc cggaaggaac acagtgggcg ctatgaatgt      960
cagggcctgg acttggacac catgatatcg ctgctgagtg aaccacagga actactggtg     1020
aactatgtgt ctgacgtccg agtgagtccc gcagcccctg agagacagga aggcagcagc     1080
ctcaccctga cctgtgaggc agagagtagc caggacctcg agttccagtg gctgagagaa     1140
gagacaggcc aggtgctgga agggggcct gtgcttcagt tgcatgacct gaaacgggag      1200
gcaggaggcg gctatcgctg cgtggcgtct gtgcccagca tacccggcct gaaccgcaca     1260
cagctggtca acgtggccat ttttggcccc ccttggatgg cattcaagga gaggaaggtg     1320
tgggtgaaag agaatatggt gttgaatctg tcttgtgaag cgtcagggca ccccggccc      1380 accatctcct ggaacgtcaa cggcacggca agtgaacaag accaagatcc acagcgagtc     1440
ctgagcaccc tgaatgtcct cgtgaccccg gagctgttgg agacaggtgt tgaatgcacg     1500
gcctccaacg acctgggcaa aaacaccagc atcctcttcc tggagctggt caatttaacc     1560
accctcacac cagactccaa cacaaccact ggcctcagca cttccactgc cagtcctcat     1620
accagagcca acagcacctc cacagagaga aagctg                               1656
```

<210> SEQ ID NO 11
<211> LENGTH: 1659
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146 protein (2)

<400> SEQUENCE: 11

```
atggggcttc ccaggctggt ctgcgccttc ttgctcgccg cctgctgctg ctgtcctcgc       60
gtcgcgggtg tgcccggaga ggctgagcag cctgcgcctg agctggtgga ggtggaagtg      120
ggcagcacag cccttctgaa gtgcggcctc tcccagtccc aaggcaacct cagccatgtc      180 gactggttttt ctgtccacaa ggagaagcgg acgctcatct ccgtgtgcg ccagggccag      240 ggccagagcg aacctgggga gtacgagcag cggctcagcc tccaggacag aggggctact      300 ctggcccctga ctcaagtcac ccccaagac gagcgcatct tcttgtgcca gggcaagcgc      360
cctcggtccc aggagtaccg catccagctc cgcgtctaca agctccgga ggagccaaac      420 atccaggtca acccctgggc atccctgtg aacagtaagg agcctgagga ggtcgctacc      480
tgtgtaggga ggaacgggta ccccattcct caagtcatct ggtacaagaa tggccggcct      540
ctgaaggaag agaagaaccg ggtccacatt cagtcgtccc agactgtgga gtcgagtggt     600
ttgtacacct tgcagagtat tctgaaggca cagctggtta agaagacaa agatgcccag       660 ttttactgtg agctcaacta ccggctgccc agtgggaacc acatgaagga gtccagggaa      720
gtcaccgtcc ctgttttcta cccgacagaa aaagtgtggc tggaagtgga gcccgtggga      780
atgctgaagg aaggggaccg cgtggaaatc aggtgtttgg ctgatggcaa ccctccacca      840
cacttcagca tcagcaagca gaaccccagc accaggagg cagaggaaga acaaccaac        900 gacaacgggg tcctggtgct ggagcctgcc cggaaggaac acagtgggcg ctatgaatgt      960
```

| | | | | |
|---|---|---|---|---|
| cagggcctgg | acttggacac | catgatatcg | ctgctgagtg | aaccacagga actactggtg | 1020 |
| aactatgtgt | ctgacgtccg | agtgagtccc | gcagccctg | agagacagga aggcagcagc | 1080 |
| ctcaccctga | cctgtgaggc | agagagtagc | caggacctcg | agttccagtg gctgagagaa | 1140 |
| gagacaggcc | aggtgctgga | aagggggcct | gtgcttcagt | tgcatgacct gaaacgggag | 1200 |
| gcaggaggcg | gctatcgctg | cgtggcgtct | gtgcccagca | tacccggcct gaaccgcaca | 1260 |
| cagctggtca | acgtggccat | ttttggcccc | ccttggatgg | cattcaagga gaggaaggtg | 1320 |
| tgggtgaaag | agaatatggt | gttgaatctg | tcttgtgaag | cgtcagggca ccccggccc | 1380 |
| accatctcct | ggaacgtcaa | cggcacggca | agtgaacaag | accaagatcc acagcgagtc | 1440 |
| ctgagcaccc | tgaatgtcct | cgtgaccccg | gagctgttgg | agacaggtgt tgaatgcacg | 1500 |
| gcctccaacg | acctgggcaa | aaacaccagc | atcctcttcc | tggagctggt caatttaacc | 1560 |
| accctcacac | cagactccaa | cacaaccact | ggcctcagca | cttccactgc cagtcctcat | 1620 |
| accagagcca | acagcacctc | cacagagaga | aagctgccg |  | 1659 |

<210> SEQ ID NO 12
<211> LENGTH: 1662
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146 protein (3)

<400> SEQUENCE: 12

| | | | | |
|---|---|---|---|---|
| atggggcttc | ccaggctggt | ctgcgccttc | ttgctcgccg | cctgctgctg ctgtcctcgc | 60 |
| gtcgcgggtg | tgcccggaga | ggctgagcag | cctgcgcctg | agctggtgga ggtggaagtg | 120 |
| ggcagcacag | cccttctgaa | gtgcggcctc | tcccagtccc | aaggcaacct cagccatgtc | 180 |
| gactggtttt | ctgtccacaa | ggagaagcgg | acgctcatct | tccgtgtgcg ccagggccag | 240 |
| ggccagagcg | aacctgggga | gtacgagcag | cggctcagcc | tccaggacag aggggctact | 300 |
| ctggccctga | ctcaagtcac | cccccaagac | gagcgcatct | tcttgtgcca gggcaagcgc | 360 |
| cctcggtccc | aggagtaccg | catccagctc | cgcgtctaca | agctccggag ggagccaaac | 420 |
| atccaggtca | ccccctgggg | catccctgtg | aacagtaagg | agcctgagga ggtcgctacc | 480 |
| tgtgtaggga | ggaacgggta | ccccattcct | caagtcatct | ggtacaagaa tggccggcct | 540 |
| ctgaaggagg | agaagaaccg | ggtccacatt | cagtcgtccc | agactgtgga gtcgagtggt | 600 |
| ttgtacacct | tgcagagtat | tctgaaggca | cagctggtta | agaagacaa agatgcccag | 660 |
| tttactgtg | agctcaacta | ccggctgccc | agtgggaacc | acatgaagga gtccagggaa | 720 |
| gtcaccgtcc | ctgttttcta | cccgacagaa | aaagtgtggc | tggaagtgga gcccgtggga | 780 |
| atgctgaagg | aaggggaccg | cgtggaaatc | aggtgtttgg | ctgatggcaa ccctccacca | 840 |
| cacttcagca | tcagcaagca | gaaccccagc | caggaggg | cagaggaaga acaaccaac | 900 |
| gacaacgggg | tcctggtgct | ggagcctgcc | cggaaggaac | acagtgggcg ctatgaatgt | 960 |
| cagggcctgg | acttggacac | catgatatcg | ctgctgagtg | aaccacagga actactggtg | 1020 |
| aactatgtgt | ctgacgtccg | agtgagtccc | gcagccctg | agagacagga aggcagcagc | 1080 |
| ctcaccctga | cctgtgaggc | agagagtagc | caggacctcg | agttccagtg gctgagagaa | 1140 |
| gagacaggcc | aggtgctgga | aagggggcct | gtgcttcagt | tgcatgacct gaaacgggag | 1200 |
| gcaggaggcg | gctatcgctg | cgtggcgtct | gtgcccagca | tacccggcct gaaccgcaca | 1260 |
| cagctggtca | acgtggccat | ttttggcccc | ccttggatgg | cattcaagga gaggaaggtg | 1320 |

-continued

```
tgggtgaaag agaatatggt gttgaatctg tcttgtgaag cgtcaggca ccccggccc     1380
accatctcct ggaacgtcaa cggcacggca agtgaacaag accaagatcc acagcgagtc   1440
ctgagcaccc tgaatgtcct cgtgaccccg gagctgttgg agacaggtgt tgaatgcacg   1500
gcctccaacg acctgggcaa aaacaccagc atcctcttcc tggagctggt caatttaacc   1560
accctcacac cagactccaa cacaaccact ggcctcagca cttccactgc cagtcctcat   1620
accagagcca acagcacctc cacagagaga aagctgccgg ag                      1662
```

<210> SEQ ID NO 13
<211> LENGTH: 1665
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146 protein (4)

<400> SEQUENCE: 13

```
atggggcttc ccaggctggt ctgcgccttc ttgctcgccg cctgctgctg ctgtcctcgc     60
gtcgcgggtg tgcccggaga ggctgagcag cctgcgcctg agctggtgga ggtggaagtg   120
ggcagcacag cccttctgaa gtgcggcctc tcccagtccc aaggcaacct cagccatgtc   180
gactggtttt ctgtccacaa ggagaagcgg acgctcatct ccgtgtgcg ccagggccag   240
ggccagagcg aacctgggga gtacgagcag cggctcagcc tccaggacag aggggctact   300
ctggccctga ctcaagtcac cccccaagac gagcgcatct tcttgtgcca gggcaagcgc   360
cctcggtccc aggagtaccg catccagctc cgcgtctaca agctccgga ggagccaaac   420
atccaggtca cccccctggg catccctgtg aacagtaagg agcctgagga ggtcgctacc   480
tgtgtaggga ggaacgggta cccccattcct caagtcatct ggtacaagaa tggccggcct   540
ctgaaggagg agaagaaccg ggtccacatt cagtcgtccc agactgtgga gtcgagtggt   600
ttgtacacct tgcagagtat tctgaaggca cagctggtta aagaagacaa agatgcccag   660
ttttactgtg agctcaacta ccggctgccc agtgggaacc acatgaagga gtccagggaa   720
gtcaccgtcc ctgttttcta cccgacagaa aaagtgtggc tggaagtgga gcccgtggga   780
atgctgaagg aaggggaccg cgtgaaaatc aggtgtttgg ctgatggcaa ccctccacca   840
cacttcagca tcagcaagca gaaccccagc accaggagg cagaggaaga acaaccaac    900
gacaacgggg tcctggtgct ggagcctgcc cggaaggaac acagtgggcg ctatgaatgt   960
cagggcctgg acttggacac catgatatcg ctgctgagtg aaccacagga actactggtg   1020
aactatgtgt ctgacgtccg agtgagtccc gcagcccctg agagacagga aggcagcagc   1080
ctcaccctga cctgtgaggc agagagtagc caggacctcg agttccagtg gctgagagaa   1140
gagacaggcc aggtgctgga aggggggcct gtgcttcagt tgcatgacct gaaacgggag   1200
gcaggaggcg gctatcgctg cgtggcgtct gtgcccagca tacccggcct gaaccgcaca   1260
cagctggtca acgtggccat ttttggcccc ccttggatgg cattcaagga gaggaaggtg   1320
tgggtgaaag agaatatggt gttgaatctg tcttgtgaag cgtcaggca ccccggccc    1380
accatctcct ggaacgtcaa cggcacggca agtgaacaag accaagatcc acagcgagtc   1440
ctgagcaccc tgaatgtcct cgtgaccccg gagctgttgg agacaggtgt tgaatgcacg   1500
gcctccaacg acctgggcaa aaacaccagc atcctcttcc tggagctggt caatttaacc   1560
accctcacac cagactccaa cacaaccact ggcctcagca cttccactgc cagtcctcat   1620
```
accagagcca acagcacctc cacagagaga aagctgccgg agccg    1665

<210> SEQ ID NO 14
<211> LENGTH: 1668
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146
      protein (5)

<400> SEQUENCE: 14

```
atgggcttc ccaggctggt ctgcgccttc ttgctcgccg cctgctgctg ctgtcctcgc    60
gtcgcgggtg tgcccggaga ggctgagcag cctgcgcctg agctggtgga ggtggaagtg   120
ggcagcacag cccttctgaa gtgcggcctc tcccagtccc aaggcaacct cagccatgtc   180
gactggtttt ctgtccacaa ggagaagcgg acgctcatct ccgtgtgcg ccagggccag    240
ggccagagcg aacctgggga gtacgagcag cggctcagcc tccaggacag aggggctact   300
ctggccctga ctcaagtcac cccccaagac gagcgcatct tcttgtgcca gggcaagcgc   360
cctcggtccc aggagtaccg catccagctc cgcgtctaca agctccgga ggagccaaac    420
atccaggtca ccccctggg catccctgtg aacagtaagg agcctgagga ggtcgctacc   480
tgtgtaggga ggaacgggta ccccattcct caagtcatct ggtacaagaa tggccggcct   540
ctgaaggagg agaagaaccg ggtccacatt cagtcgtccc agactgtgga gtcgagtggt   600
ttgtacacct tgcagagtat tctgaaggca cagctggtta agaagacaa agatgcccag    660
ttttactgtg agctcaacta ccggctgccc agtgggaacc acatgaagga gtccagggaa   720
gtcaccgtcc ctgttttcta cccgacagaa aaagtgtggc tggaagtgga gcccgtggga   780
atgctgaagg aaggggaccg cgtggaaatc aggtgtttgg ctgatggcaa ccctccacca   840
cacttcagca tcagcaagca gaaccccagc accagggagg cagaggaaga gacaaccaac   900
gacaacgggg tcctggtgct ggagcctgcc cggaaggaac acagtgggcg ctatgaatgt   960
cagggcctgg acttggacac catgatatcg ctgctgagtg aaccacagga actactggtg  1020
aactatgtgt ctgacgtccg agtgagtccc gcagccctg agagacagga aggcagcagc   1080
ctcaccctga cctgtgaggc agagagtagc caggacctcg agttccagtg gctgagagaa  1140
gagacaggcc aggtgctgga aagggggcct gtgcttcagt tgcatgacct gaaacgggag  1200
gcaggaggcg gctatcgctg cgtggcgtct gtgcccagca tacccggcct gaaccgcaca  1260
cagctggtca acgtggccat ttttggcccc ccttggatgg cattcaagga gaggaaggtg  1320
tgggtgaaag agaatatggt gttgaatctg tcttgtgaag cgtcagggca ccccggccc   1380
accatctcct ggaacgtcaa cggcacggca agtgaacaag accaagatcc acagcgagtc  1440
ctgagcaccc tgaatgtcct cgtgaccccg gagctgttgg agacaggtgt tgaatgcacg  1500
gcctccaacg acctgggcaa aaacaccagc atcctcttcc tggagctggt caatttaacc  1560
accctcacac cagactccaa cacaaccact ggcctcagca cttccactgc cagtcctcat  1620
accagagcca acagcacctc cacagagaga aagctgccgg agccggag              1668
```

<210> SEQ ID NO 15
<211> LENGTH: 1671
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146
      protein (6)

<400> SEQUENCE: 15

```
atgggcttc ccaggctggt ctgcgccttc ttgctcgccg cctgctgctg ctgtcctcgc      60
gtcgcgggtg tgcccggaga ggctgagcag cctgcgcctg agctggtgga ggtggaagtg     120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag     240 ggccagagcg aacctgggga gtacgagcag cggctcagcc tccaggacag aggggctact   300
ctggccctga ctcaagtcac cccccaagac gagcgcatct tcttgtgcca gggcaagcgc   360
cctcggtccc aggagtaccg catccagctc cgcgtctaca agctccgga ggagccaaac    420 atccaggtca ccccctggg catccctgtg aacagtaagg agcctgagga ggtcgctacc    480
tgtgtaggga ggaacgggta ccccattcct caagtcatct ggtacaagaa tggccggcct   540
ctgaaggagg agaagaaccg ggtccacatt cagtcgtccc agactgtgga gtcgagtggt   600
ttgtacacct tgcagagtat tctgaaggca cagctggtta agaagacaa agatgcccag    660 ttttactgtg agctcaacta ccggctgccc agtgggaacc acatgaagga gtccagggaa  720
gtcaccgtcc ctgttttcta cccgacagaa aaagtgtggc tggaagtgga gcccgtggga   780
atgctgaagg aaggggaccg cgtggaaatc aggtgtttgg ctgatggcaa ccctccacca   840
cacttcagca tcagcaagca gaaccccagc caccaggagg cagaggaaga gacaaccaac   900
gacaacgggg tcctggtgct ggagcctgcc cggaaggaac acagtgggcg ctatgaatgt   960
cagggcctgg acttggacac catgatatcg ctgctgagtg aaccacagga actactggtg  1020
aactatgtgt ctgacgtccg agtgagtccc gcagccctg agagacagga aggcagcagc  1080
ctcaccctga cctgtgaggc agagagtagc caggacctcg agttccagtg gctgagagaa  1140
gagacaggcc aggtgctgga aagggggcct gtgcttcagt gcatgacct gaaacgggag  1200 gcaggaggcg gctatcgctg cgtggcgtct gtgcccagca tacccggcct gaaccgcaca  1260
cagctggtca acgtggccat ttttggcccc ccttggatgg cattcaagga gaggaaggtg  1320
tgggtgaaag agaatatggt gttgaatctg tcttgtgaag cgtcagggca ccccggccc   1380 accatctcct ggaacgtcaa cggcacggca agtgaacaag accaagatcc acagcgagtc  1440
ctgagcaccc tgaatgtcct cgtgaccccg gagctgttgg agacaggtgt tgaatgcacg  1500
gcctccaacg acctgggcaa aaacaccagc atcctcttcc tggagctggt caatttaacc  1560 acccctcacac cagactccaa cacaaccact ggcctcagca cttccactgc cagtcctcat  1620
accagagcca acagcaccct cacagagaga aagctgccgg agccggagag c            1671
```

<210> SEQ ID NO 16
<211> LENGTH: 1674
<212> TYPE: DNA
<213> ORGANISM: Homo sapiens
<220> FEATURE:
<221> NAME/KEY: misc_feature
<223> OTHER INFORMATION: Nucleic acid sequence of human soluble CD146 protein (7)

<400> SEQUENCE: 16

```
atgggcttc ccaggctggt ctgcgccttc ttgctcgccg cctgctgctg ctgtcctcgc      60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag     240
```

| | |
|---|---|
| ggccagagcg aacctgggga gtacgagcag cggctcagcc tccaggacag aggggctact | 300 |
| ctggccctga ctcaagtcac cccccaagac gagcgcatct tcttgtgcca gggcaagcgc | 360 |
| cctcggtccc aggagtaccg catccagctc cgcgtctaca aagctccgga ggagccaaac | 420 |
| atccaggtca ccccctggg catccctgtg aacagtaagg agcctgagga ggtcgctacc | 480 |
| tgtgtaggga ggaacgggta ccccattcct caagtcatct ggtacaagaa tggccggcct | 540 |
| ctgaaggagg agaagaaccg ggtccacatt cagtcgtccc agactgtgga gtcgagtggt | 600 |
| ttgtacacct tgcagagtat tctgaaggca cagctggtta agaagacaa agatgcccag | 660 |
| ttttactgtg agctcaacta ccggctgccc agtgggaacc acatgaagga gtccagggaa | 720 |
| gtcaccgtcc ctgtttttcta cccgacagaa aaagtgtggc tggaagtgga gcccgtggga | 780 |
| atgctgaagg aaggggaccg cgtggaaatc aggtgtttgg ctgatggcaa ccctccacca | 840 |
| cacttcagca tcagcaagca gaaccccagc accagggagg cagaggaaga gacaaccaac | 900 |
| gacaacgggg tcctggtgct ggagcctgcc cggaaggaac acagtgggcg ctatgaatgt | 960 |
| cagggcctgg acttggacac catgatatcg ctgctgagtg aaccacagga actactggtg | 1020 |
| aactatgtgt ctgacgtccg agtgagtccc gcagccctg agagacagga aggcagcagc | 1080 |
| ctcaccctga cctgtgaggc agagagtagc caggacctcg agttccagtg gctgagagaa | 1140 |
| gagacaggcc aggtgctgga aggggggcct gtgcttcagt tgcatgacct gaaacgggag | 1200 |
| gcaggaggcg gctatcgctg cgtggcgtct gtgcccagca tacccggcct gaaccgcaca | 1260 |
| cagctggtca acgtggccat ttttggcccc ccttggatgg cattcaagga gaggaaggtg | 1320 |
| tgggtgaaag agaatatggt gttgaatctg tcttgtgaag cgtcagggca ccccggccc | 1380 |
| accatctcct ggaacgtcaa cggcacggca agtgaacaag accaagatcc acagcgagtc | 1440 |
| ctgagcaccc tgaatgtcct cgtgacccg gagctgttgg agacaggtgt tgaatgcacg | 1500 |
| gcctccaacg acctgggcaa aaacaccagc atcctcttcc tggagctggt caatttaacc | 1560 |
| accctcacac cagactccaa cacaaccact ggcctcagca cttccactgc cagtcctcat | 1620 |
| accagagcca acagcacctc cacagagaga aagctgccgg agccggagag ccgg | 1674 |

<210> SEQ ID NO 17
<211> LENGTH: 1815
<212> TYPE: DNA
<213> ORGANISM: Homo sapiens
<220> FEATURE:
<221> NAME/KEY: misc_feature
<223> OTHER INFORMATION: Nucleic acid sequence of human short CD146
    protein

<400> SEQUENCE: 17

| | |
|---|---|
| atggggcttc ccaggctggt ctgcgccttc ttgctcgccg cctgctgctg ctgtcctcgc | 60 |
| gtcgcgggtg tgcccggaga ggctgagcag cctgcgcctg agctggtgga ggtggaagtg | 120 |
| ggcagcacag cccttctgaa gtgcggcctc tcccagtccc aaggcaacct cagccatgtc | 180 |
| gactggtttt ctgtccacaa ggagaagcgg acgctcatct ccgtgtgcg ccagggccag | 240 |
| ggccagagcg aacctgggga gtacgagcag cggctcagcc tccaggacag aggggctact | 300 |
| ctggccctga ctcaagtcac cccccaagac gagcgcatct tcttgtgcca gggcaagcgc | 360 |
| cctcggtccc aggagtaccg catccagctc cgcgtctaca aagctccgga ggagccaaac | 420 |
| atccaggtca ccccctggg catccctgtg aacagtaagg agcctgagga ggtcgctacc | 480 |
| tgtgtaggga ggaacgggta ccccattcct caagtcatct ggtacaagaa tggccggcct | 540 |
| ctgaaggagg agaagaaccg ggtccacatt cagtcgtccc agactgtgga gtcgagtggt | 600 |

```
ttgtacacct tgcagagtat tctgaaggca cagctggtta agaagacaa agatgcccag      660 ttttactgtg agctcaacta ccggctgccc agtgggaacc acatgaagga gtccagggaa      720
gtcaccgtcc ctgttttcta cccgacagaa aaagtgtggc tggaagtgga gcccgtggga      780
atgctgaagg aaggggaccg cgtggaaatc aggtgtttgg ctgatggcaa ccctccacca      840
cacttcagca tcagcaagca gaaccccagc accagggagg cagaggaaga gacaaccaac      900
gacaacgggg tcctggtgct ggagcctgcc cggaaggaac acagtgggcg ctatgaatgt      960
cagggcctgg acttggacac catgatatcg ctgctgagtg aaccacagga actactggtg     1020
aactatgtgt ctgacgtccg agtgagtccc gcagcccctg agacagga aggcagcagc      1080 ctcaccctga cctgtgaggc agagagtagc caggacctcg agttccagtg gctgagagaa     1140
gagacaggcc aggtgctgga agggggcct gtgcttcagt tgcatgacct gaaacgggag     1200
gcaggaggcg gctatcgctg cgtggcgtct gtgcccagca tacccggcct gaaccgcaca     1260
cagctggtca acgtggccat ttttggcccc ccttggatgg cattcaagga gaggaaggtg     1320
tgggtgaaag agaatatggt gttgaatctg tcttgtgaag cgtcagggca ccccggccc      1380 accatctcct ggaacgtcaa cggcacggca agtgaacaag accaagatcc acagcgagtc     1440
ctgagcaccc tgaatgtcct cgtgaccccg agctgttgg agacaggtgt tgaatgcacg     1500
gcctccaacg acctgggcaa aaacaccagc atcctcttcc tggagctggt caatttaacc     1560
accctcacac cagactccaa cacaaccact ggcctcagca cttccactgc cagtcctcat     1620
accagagcca acagcacctc cacagagaga aagctgccgg agccggagag ccggggcgtg     1680
gtcatcgtgg ctgtgattgt gtgcatcctg gtcctggcgg tgctgggcgc tgtcctctat     1740
ttcctctata agaagggcaa gctgccgtgc aggagctcag ggaagcagga gatggagaga     1800
aatacatcga tctga                                                     1815
```

<210> SEQ ID NO 18
<211> LENGTH: 20
<212> TYPE: DNA
<213> ORGANISM: Artificial sequence
<220> FEATURE:
<223> OTHER INFORMATION: UPA _ Forward specific primer sequence

<400> SEQUENCE: 18
tttgcggcca tctacaggag                                                 20

<210> SEQ ID NO 19
<211> LENGTH: 21
<212> TYPE: DNA
<213> ORGANISM: Artificial sequence
<220> FEATURE:
<223> OTHER INFORMATION: UPA _ Reverse specific primer sequence

<400> SEQUENCE: 19
agttaagcct tgagcgaccc a                                               21

<210> SEQ ID NO 20
<211> LENGTH: 22
<212> TYPE: DNA
<213> ORGANISM: Artificial sequence
<220> FEATURE:
<223> OTHER INFORMATION: KDR _ Forward specific primer sequence

<400> SEQUENCE: 20
tgtgggtttg cctagtgttt ct                                              22

<210> SEQ ID NO 21
<211> LENGTH: 21
<212> TYPE: DNA
<213> ORGANISM: Artificial sequence
<220> FEATURE:
<223> OTHER INFORMATION: KDR _ Reverse specific primer sequence

<400> SEQUENCE: 21
cactcagtca cctccaccct t                                             21

<210> SEQ ID NO 22
<211> LENGTH: 18
<212> TYPE: DNA
<213> ORGANISM: Artificial sequence
<220> FEATURE:
<223> OTHER INFORMATION: eNOS _ Forward specific primer sequence

<400> SEQUENCE: 22
ctcatgggca cggtgatg                                                 18

<210> SEQ ID NO 23
<211> LENGTH: 24
<212> TYPE: DNA
<213> ORGANISM: Artificial sequence
<220> FEATURE:
<223> OTHER INFORMATION: eNOS _ Reverse specific primer sequence

<400> SEQUENCE: 23
accacgtcat actcatccat acac                                          24

<210> SEQ ID NO 24
<211> LENGTH: 24
<212> TYPE: DNA
<213> ORGANISM: Artificial sequence
<220> FEATURE:
<223> OTHER INFORMATION: MMP2 _ Forward specific primer sequence

<400> SEQUENCE: 24
tgatcttgac cagaatacca tcga                                          24

<210> SEQ ID NO 25
<211> LENGTH: 20
<212> TYPE: DNA
<213> ORGANISM: Artificial sequence
<220> FEATURE:
<223> OTHER INFORMATION: MMP2 _ Reverse specific primer sequence

<400> SEQUENCE: 25
ggcttgcgag ggaagaagtt                                               20

<210> SEQ ID NO 26
<211> LENGTH: 10
<212> TYPE: PRT
<213> ORGANISM: Artificial sequence
<220> FEATURE:
<223> OTHER INFORMATION: Artificial sequence

<400> SEQUENCE: 26

Glu Gln Lys Leu Ile Ser Glu Glu Asp Leu
1               5                   10

HUMAN SOLUBLE CD146, PREPARATION AND USES THEREOF

CROSS-REFERENCE TO RELATED APPLICATION

This application is the U.S. national stage application of International Patent Application No. PCT/EP2010/051080, filed Jan. 29, 2010.

FIELD OF THE INVENTION

The present invention relates to compositions and methods for modulating angiogenesis in vivo, ex vivo or in vitro.

More particularly, the invention relates to soluble CD146 proteins usable in the context of human therapy, as well as to corresponding antibodies. Particular forms of CD146, herein described, may be used to mobilize, in vivo or ex vivo, both mature and immature endothelial cells, as well as to increase their influence on angiogenesis. They can further be used to prepare compositions, in particular pharmaceutical, diagnostic or cosmetic compositions, and corresponding kits.

The invention further relates to methods of therapy or diagnosis, and to cosmetic treatments, using the previously mentioned compounds, compositions and cells.

BACKGROUND OF THE INVENTION

The formation of new blood vessels either from differentiating endothelial cells during embryonic development (vasculogenesis) or from pre-existing vessels during adult life (angiogenesis) is an essential feature of organ development, reproduction, and wound healing in higher organisms.

Therapeutic angiogenesis is an effective means to treat patients suffering from a disease or a disorder leading to tissue ischemia.

Treatment of ischemia, using non-surgical therapy, has become possible with the discovery of angiogenic factors favouring formation of new blood vessels. Several candidate angiogenic factors have been described so far which were the subject of clinical trials.

Enthusiasm has however been hampered by series of negative clinical outcomes. Regarding VEGF for example, despite the potent angiogenic effects of this factor, its expression did not efficiently improve muscle blood flow in patients. This was explained by the formation of leaky vascular lacunae and arteriovenous shunts interfering with the downstream microcirculation.

Endothelial progenitor cells (EPCs) have been identified in adult human peripheral blood, in bone marrow and in cord blood (Asahara T, Murohara T, Sullivan A, Silver M, van der Zee R, Li T,Witzenbichler B, Schatteman G, Isner J M. Isolation of putative progenitor endothelial cells for angiogenesis. Science. 1997 275:964-7). Circulating EPCs participate in postnatal neovascularization after mobilization from the bone marrow. Transplantation of culture-expanded EPCs, obtained either from blood or from autologous bone marrow mononuclear cells, was found to be able to augment ischemia-induced neovascularization in vivo.

The use of cultured cells as a therapeutic approach in patients is however considerably limited by the small proportion of EPCs in the peripheral blood, the necessity of harvesting a large amount of bone marrow to isolate a sufficient number of EPCs, and the heterogeneity of the recovered EPCs.

Despite their drawbacks, the use of angiogenic growth factors thus remains to date the primary strategy of therapeutic angiogenesis for the treatment of patients, such as patients presenting with severe peripheral arterial disease (also called peripheral vascular disease) or ischemic heart disease.

CD146, also known as MCAM, MUC18, or Mel-CAM, is a component of the endothelial junction which belongs to the immunoglobulin superfamily (Bardin N, Anfosso F, Massé J M, Cramer E, Sabatier F, Le Bivic A, Sampol J, Dignat-George F. Identification of CD146 as a component of the endothelial junction involved in the control of cell-cell cohesion. Blood. 2001; 98:3677-84). As a member of such a family, it consists in five Ig domains, a transmembrane domain, and a cytoplasmic region.

CD146 is mainly known to occur in two distinct forms differing by the length of their cytoplasmic domain: a long isoform (herein identified as "long CD146") and a short isoform (herein identified as "short CD146"), both present in the membrane of cells, mainly endothelial cells.

CD146 is involved in the control of cell and tissue architecture, as demonstrated by the regulation of its expression during endothelium monolayer formation, its involvement in the control of paracellular permeability (Bardin N, Anfosso F, Massé J M, Cramer E, Sabatier F, Le Bivic A, Sampol J,Dignat-George F. Identification of CD146 as a component of the endothelial junction involved in the control of cell-cell cohesion. Blood. 2001; 98:3677-84) and its colocalization with the actin cytoskeleton (Anfosso F, Bardin N, Vivier E, Sabatier F, Sampol J, Dignat-George F. Outside-in signaling pathway linked to CD146 engagement in human endothelial cells. J Biol Chem. 2001; 276:1564-9).

Membranous CD146 has been reported to promote tumor growth, angiogenesis, and metastasis in human melanoma. Membranous CD146 expression levels and distribution are closely associated with tumor progression and onset of metastasis in human malignant melanoma. Anti-membranous CD146 antibodies have been described as capable of significantly inhibiting the growth and metastasic properties of human melanoma cells in nude mice (Mills L, Tellez C, Huang S, Baker C, McCarty M, Green L, Gudas J M, Feng X, Bar-Eli M. Fully human antibodies to MCAM/MUC18 inhibit tumor growth and metastasis of human melanoma. Cancer Res. 2002; 62:5106-14.). Membranous CD146 has been shown to display angiogenic properties, both in an in vitro model of human umbilical vein endothelial cells (HU-VEC) (Kang Y, Wang F, Feng J, Yang D, Yang X, Yan X. Knockdown of CD146 reduces the migration and proliferation of human endothelial cells. Cell Res. 2006; 16(3):313-8) and in in vivo models of chicken chorioallantoic membrane (CAM) assays and tumor growth in mice (Yan X, Lin Y, Yang D, Shen Y, Yuan M, Zhang Z, Li P, Xia H, Li L, Luo D, Liu Q, Mann K, Bader B L. A novel anti-CD146 monoclonal antibody, AA98, inhibits angiogenesis and tumor growth Blood. 2003;102:184-91). mAb AA98 has been shown by Yan et al. to display a remarkably restricted immunoreactivity against intratumoral vasculature compared with blood vessels of normal tissues.

Finally, inventors recently showed that CD146 was involved in the regulation of monocytes transendothelial migration (CD146 and its soluble form regulate monocytes transendothelial migration. Arteriosclerosis, thrombosis and Vascular Biology, 2009; 29: 746-53).

Different localisations and functional differences have been identified in the literature for the two membranous isoforms of chicken CD146. In one study, authors analyzed chicken CD146 targeting in polarized epithelial Madin- Darby canine kidney (MDCK) cells using CD146-GFP chimeras, to identify the respective role of each isoform. They showed by confocal microscopy that short CD146 and long CD146 were addressed to the apical and basolateral membranes, respectively (Guezguez B, Vigneron P, Alais S, Jaffredo T, Gavard J, Mège R M, Dunon D. A dileucine motif targets MCAM-1 cell adhesion molecule to the basolateral membrane in MDCK cells. FEBS Lett. 2006; 580:3649-56). In another study, the same group showed that long CD146 promoted rolling via microvilli induction in lymphocytes and displayed adhesion receptor activity, suggesting its involvement in the recruitment of activated T cells to inflammation sites (Guezguez B, Vigneron P, Lamerant N, Kieda C, Jaffredo T, Dunon D. Dual role of melanoma cell adhesion molecule (MCAM)/CD146 in lymphocyte endothelium interaction: MCAM/CD146 promotes rolling via microvilli induction in lymphocyte and is an endothelial adhesion receptor. J Immunol. 2007; 179:6673-85).

The existence of a soluble form of CD146 has been discovered initially from a western blot and its possible role as a competitive inhibitor of the CD146 membrane-bound form has been suggested (Bardin N, Francès V, Combes V, Sampol J, Dignat-George F. CD146: biosynthesis and production of a soluble form in human cultured endothelial cells. FEBS Lett. 1998; 421:12-4).

However, until now, the soluble form has not been structurally or functionally characterized. A breakthrough results from the inventors' discovery that biologically active forms of human CD146 exist not only as membrane-bound forms but also as a soluble form present in the human serum. Inventors first suggested that changes in sCD146 levels may be related to physiopathological conditions associated with alteration in endothelial barrier integrity such as permeability, leukocyte transmigration or angiogenesis (N. Bardin, F. Anfosso, V. Combes, J. Nedelec, I. Besson-Faure, P. Brunet, V. Moal, J. Sampol, and F. Dignat-George. Soluble CD146, a junctional endothelial adhesion molecule, is increased in vascular disorders, Workshop K endothelial cells; DK, vol. 55, no. SUPPL. 01, 1 Jan. 2000, page 63, ISSN: 0340-6245) and then described increased levels of sCD146 in the plasma of patients with chronic renal failure (Bardin N, Moal V, Anfosso F, Daniel L, Brunet P, Sampol J, Dignat-George F. Soluble CD146, a novel endothelial marker, is increased in physiopathological settings linked to endothelial junctional alteration, Thromb Haemost. 2003; 90:915-20). Inventors now herein describe, for the first time, the structure of said soluble forms and demonstrate (see in particular in vivo experimental results herein provided) the therapeutic properties of the human soluble CD146, in particular the angiogenic properties thereof, in contradiction with the art suggestions and in particular with previous observations from Wu Guang-JER et al. (see Wu Guang-JER et al.: "*Soluble METCAM/MUC 18 blocks angiogenesis during the in vivo tumor formation of human prostate cancer LNCaP cells.*" Proceedings of the American Association for cancer research annual meetings, vol. 47, April 2006, page 59 n & 97$^{TH}$ annual meeting of the AACR; Washington DC, USA, Apr. 01-05, 2006, ISSN: 0197-016X).

In the literature, different soluble receptors, as soluble EphB4 or soluble Notch1, have been shown to act as endogenous inhibitors of angiogenesis, acting as traps for their ligand. This is also the case for the soluble form of VEGFR2 which blocks the angiogenic effect of VEGF (Holash J, Davis S, Papadopoulos N, et al. VEGF-Trap: a VEGF blocker with potent antitumor effects. Proc Natl Acad Sci U S A. 2002; 99: 11393-8.). In contrast, other soluble molecules have been shown to act as activators of angiogenesis, such as the soluble N-cadherin fragment (Derycke L, Morbidelli L, Ziche M, et al. Soluble N-cadherin fragment promotes angiogenesis. Clin Exp Metastasis. 2006; 23: 187-201) or the soluble CD40 ligand (Melter M, Reinders M E, Sho M, et al. Ligation of CD40 induces the expression of vascular endothelial growth factor by endothelial cells and monocytes and promotes angiogenesis in vivo. Blood. 2000; 96: 3801-8.). The reason for the observed opposite effects of soluble molecules, inhibitor or activator, is unknown but may result from distinct signalling pathways. Thus, one can hypothesize that soluble forms of receptor molecules may trap the ligand and inhibit the effect. In contrast, other soluble molecules, such as soluble CD146, result from a membrane protein shedding, and could serve as a ligand that activates its receptor.

Inventors in particular herein provide new tools, using the soluble form of CD146, improving the treatment of tissue ischemia while reducing deleterious side effects observed with classically used therapies. They herein demonstrate that the soluble form of CD146 fulfills key functions in the neovascularisation process.

Inventors herein characterize the human soluble form of CD146 (herein identified as "soluble CD146") and identify amino acid sequences thereof usable in the context of a treatment. Inventors in particular describe its advantageous chemotactic and angiogenic effects on endothelial cells, in particular on endothelial progenitor cells (EPC). The human soluble form of CD146 is able to promote a therapeutic vasculogenesis and/or angiogenesis in a mammal subject, in particular in a human subject.

Other advantages of the products and compositions herein described are further indicated below.

SUMMARY OF THE INVENTION

Inventors herein demonstrate for the first time that human soluble CD146 induces the migration ability or mobilisation (chemotactic activity) and activation of endothelial cells, in particular endothelial progenitor cells, of smooth muscle cells and of hematopoietic cells, and that this molecule is able to promote vasculogenesis and/or angiogenesis in vivo. This molecule which may be administered either alone or in combination with another angiogenic factor and/or with a mature or immature endothelial cell, is an advantageous tool for therapeutic angiogenesis in patients presenting with tissue ischemia or at risk of developing such a tissue ischemia.

The present invention in particular provides a novel protein, the human soluble CD146, herein identified as "soluble CD146". This protein is naturally present in the human serum and biologically active forms thereof have been isolated by inventors and are herein provided.

In one aspect, the invention describes an isolated human soluble CD146 protein containing about 558 amino acids, preferably about 552 to about 558 amino acids, even more preferably 557, 556, 555, 554, 553 or 552 amino acids.

In a particular embodiment, the invention provides a human soluble CD146 protein usable in the context of a mammal treatment, in particular a human treatment, as herein described, comprising an amino acid sequence consisting in a sequence selected from SEQ ID NO: 1, SEQ ID NO: 2, SEQ ID NO: 3, SEQ ID NO: 4, SEQ ID NO: 5, SEQ ID NO: 6, and SEQ ID NO: 7.

In another aspect, the invention provides a composition comprising a soluble CD146 protein as herein described and a pharmaceutically acceptable carrier. In another aspect, this composition further comprises a mature or immature endothelial cell, in particular an endothelial progenitor cell, and/or another angiogenic factor.

A pharmaceutical composition according to the present invention may also comprise, as the only biologically active agent, a mature or immature endothelial cell which has been contacted with a human soluble CD146 protein and/or which has been genetically modified to express a human short or soluble CD 146 protein.

In a further aspect, the invention relates to a protein or a composition as herein described for use in the treatment or in the diagnosis of a disease, disorder or dysfunctional state leading to tissue ischemia or characterized by a decreased activation of a receptor for CD146, in particular soluble CD146, or by a decreased expression of a gene selected from the gene encoding e-NOS, uPa, MMP-2 and KDR, compared to standard expression, or for use in the prevention of ischemia.

In particular, the invention relates to the use of a protein or a composition as herein described to prepare a composition for diagnosing, preventing or treating a disease, a disorder or a dysfunctional state as herein identified.

In a particular embodiment, the invention provides a method of diagnosing, preventing or treating a disease, a disorder or a dysfunctional state in a mammal, preferably a human, as herein identified, in particular a method of diagnosing cancer (for example breast cancer, melanoma, etc.), or a method of preventing or treating a tissue ischemia.

The method of diagnosing cancer preferably comprises a step of dosing, in the mammal serum, the amount of soluble CD146 protein.

The method of preventing or treating a tissue ischemia preferably comprises a step of administering to the mammal, an effective amount of a composition, as herein described, in particular a method comprising a soluble CD146 protein.

In a further aspect, the invention relates to the use of a protein or a composition as herein described to improve the aesthetic appearance of a scar or, in prevention, to facilitate the cicatrization or healing of a wound, a cut or an incision.

An object of the present invention is a protein or a composition as herein described for use in the cicatrization of a mammal epithelium, in particular a human epithelium, in particular following a wound, a cut or an incision or in the context of a skin graft.

Another object of the present invention is a protein or a composition as herein described for use in the prevention or treatment of an eschar or a bedsore in a mammal, in particular a human.

A further object of the present invention is a protein or a composition as herein described for use in the in the context of a skin graft in a mammal, in particular a human.

A monoclonal antibody which selectively binds to the human soluble CD146 protein comprising an amino acid sequence consisting in a sequence selected from SEQ ID NO: 1, SEQ ID NO: 2, SEQ ID NO: 3, SEQ ID NO: 4, SEQ ID NO: 5, SEQ ID NO: 6 and SEQ ID NO: 7, is further herein provided. This antibody preferably also neutralizes a biological activity of the human soluble CD146 protein of the invention. Preferably, the antibody decreases or inhibits neovascularization, vascular permeability and/or vascular endothelial cell growth in a mammal, preferably a human.

The antibody, or a pharmaceutical composition comprising said antibody and a pharmaceutically acceptable carrier, herein disclosed, can be used in a mammal, preferably a human, for preventing or treating a disease, disorder or dysfunctional state characterized by an undesirable excessive neovascularization or vascular permeability, such as a cancer, by an overexpression or excessive activation of the soluble form of CD146 and/or of a receptor for CD146, in particular soluble CD146, or by an excessive expression of a gene selected from the gene encoding e-NOS, uPa, MMP-2 and KDR, compared to standard expression.

In a further embodiment, the invention provides isolated nucleic acid molecules encoding respectively a human soluble CD146 of the invention, the human short form of CD146, or recombinant forms thereof.

The nucleic acid molecule can be provided in a replicable vector comprising the nucleic acid molecule operably linked to control sequences recognized by a host cell transfected or transformed with the vector, in particular a mature or immature endothelial cell or a progenitor cell, preferably an endothelial progenitor cell. The invention further provides such an host cell comprising the vector or the nucleic acid molecule.

In another aspect, the present disclosure provides kits comprising any one or more of the herein-described protein, antibody, cell or compositions. Typically, the kit also comprises instructions for using the protein, antibody, cell or composition according to the disclosed methods.

LEGEND TO THE FIGURES

The patent or application file contains at least one drawing executed in color. Copies of this patent or patent application publication, with color drawing(s), will be provided by the Office upon request and payment of the necessary fee.

Figures 1B, 1C:
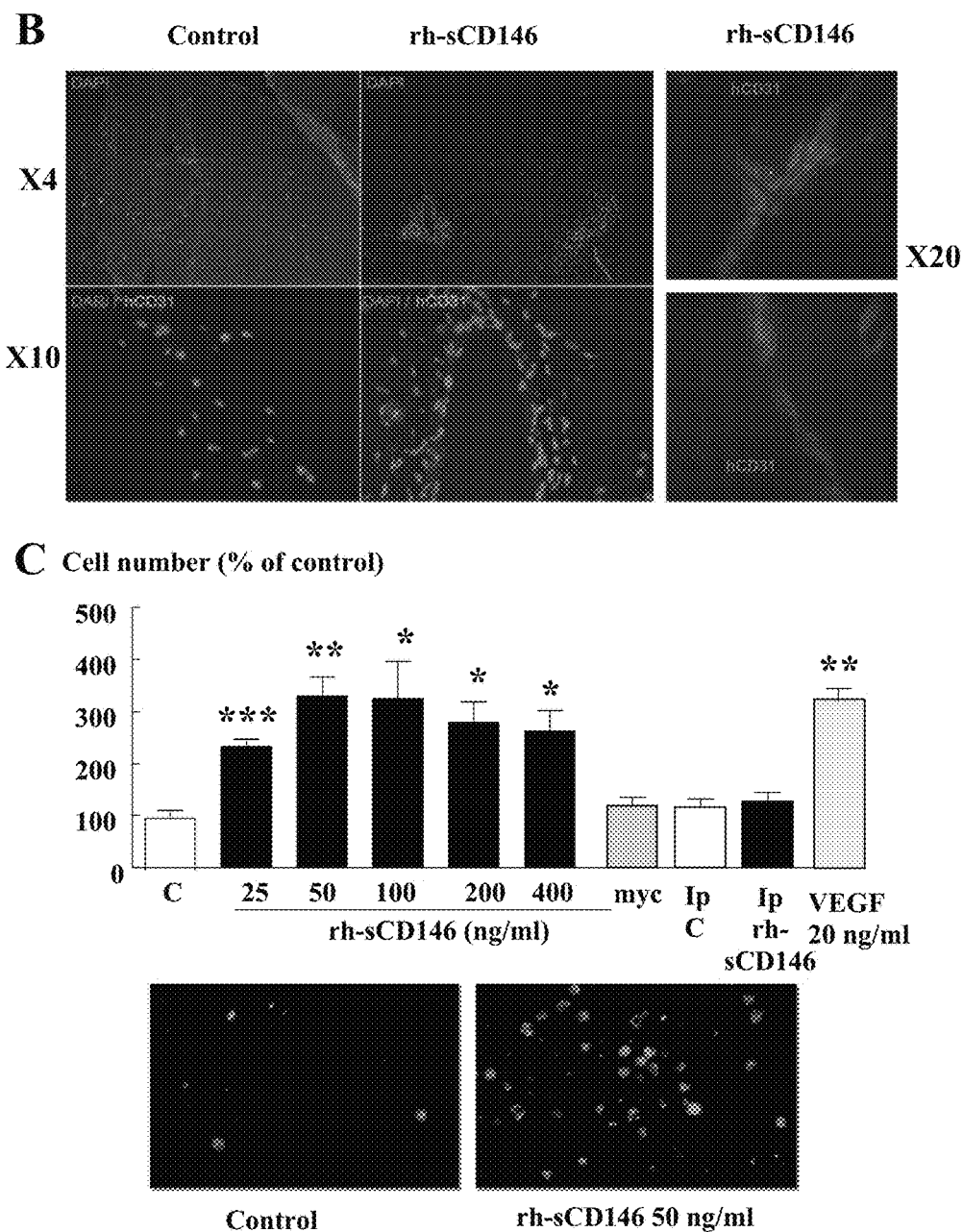
Figure 1D:
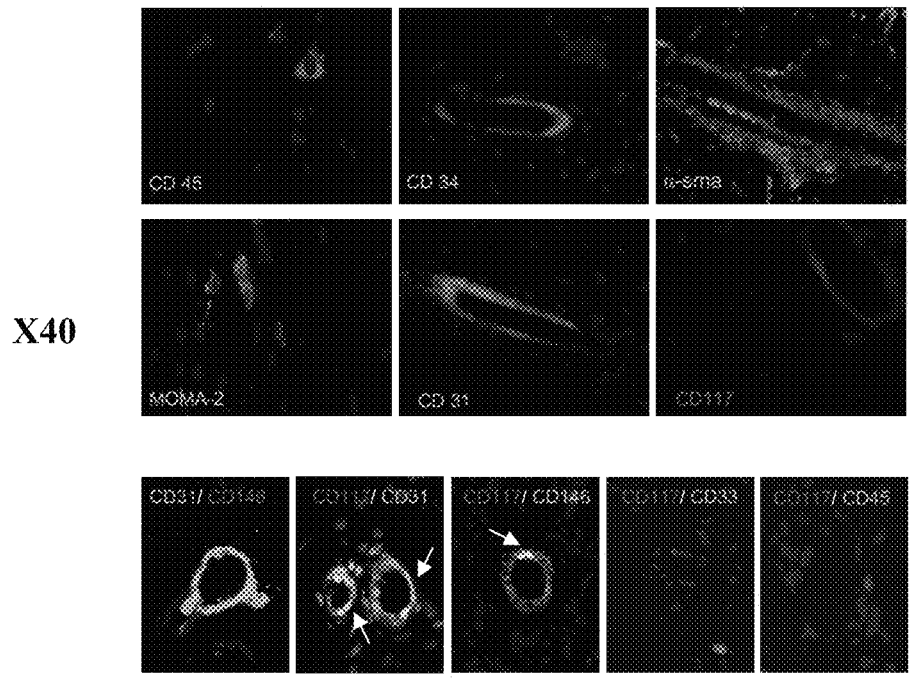

FIG. 1: Chemotactic Activity of Recombinant Human Soluble CD146 in Vivo and in Vitro.

A: Microscopic examination of Matrigel plugs maintained for 12 days in normal mice. Control Matrigel plug containing either 1 µg/R1 PBS or 1 µg/µl c-myc peptide and Matrigel plug containing 1 µg/µl rh-sCD146 (soluble DC146) were injected in the same mouse. Capillary-like structures were observed in the matrigel plugs in the presence of rh-sCD146 (arrows). Immunostaining with anti-CD31 (green) and anti-CD117 (red) antibodies in control or rh-sCD146 matrigel are shown. Nuclei were labelled with dapi (blue).

B: Immunostaining of Matrigel plugs maintained for 12 days in nude mice injected with 500,000 EPDC through the penian vein. Control Matrigel plugs containing 1 µg/µl c-myc peptide and Matrigel plugs containing 1 µg/µl rh-sCD146 were injected in the same mouse. Immunostaining was performed in matrigel plugs with anti-human CD31 (red) antibody. Cell nuclei were labelled with dapi (blue).

C: Chemotactic effect of rh-sCD146 on EPC in vitro. 200,000 EPC in EBM2 medium were seeded in the upper compartment of 8 µm pore size Transwell filters. The following agents were added at various concentrations in the medium in the lower compartment of the Transwell filter: rh-sCD146, the c-myc peptide, immunodepleted rh-sCD146 (Ip rh-sCD146), its control (IpC), or VEGF. Transwell filters were incubated overnight at 37° C. Cells were labelled with a fluorescent dye and fluorescence intensity was measured. Results are the mean values+/−SEM of 4 different experiments. *, , *: $P<0.05$, $P<0.01$, $P<0.001$, experimental vs Control.

D: Immunostainings were performed with anti-CD45, anti-CD34, anti-αsma, anti-MOMA2, anti-CD31 and anti-CD117 antibodies on sections of matrigel plugs filled with rh-sCD146 and maintained for 12 days in normal mice. Nuclei were labelled with DAPI (blue). Co-labellings were also performed with CD31/CD146, CD117/CD31, CD117/CD146, CD117/CD33 and CD117/CD45. The merge pictures are given. Yellow areas correspond to a co-labelling. In some pictures, these areas are better indicated with an arrow.

FIG. 2: Effect of Recombinant Human Soluble CD146 on Angiogenic Capacity of Endothelial Progenitor Derived Cells in Vitro A: EPC capacity to elaborate pseudo-capillaries in Matrigel plugs was evaluated in the presence or absence of different concentrations of rh-sCD146, Fc-CD146 or control IgG1, the c-myc peptide, immunodepleted rh-sCD146 (Ip rh-sCD146) or its control (IpC), or VEGF. Number of tubes was counted after 5 hours of incubation. Results are the mean values+/−SEM of 6 different experiments. *, **: P<0.05, P<0.01, experimental vs. Control.

B: The proliferation capacity of EPC was evaluated using the experimental conditions described in (A). Results are the mean values+/−SEM of 5 different experiments. , *: P<0.01, P<0.001, experimental vs. Control.

C: The migration capacity of EPC was evaluated using the experimental conditions described in (A). Results are the mean values+/−SEM of 4 different experiments. *, ***: P<0.05, P<0.001, experimental vs. Control.

FIG. 3: Upregulation of Angiogenic Gene Transcripts and Products in Endothelial Progenitor-derived Cells in Response to Recombinant Human Soluble CD146

A: Alterations in gene expression profiles were monitored in EPC treated or not with 50 ng/ml rh-sCD146 for 3 h using oligo-arrays specific for angiogenic pathways. Gene expression alterations were confirmed by qPCR. Results are mean value of 4 different experiments. *, **: P<0.05, P<0.01, experimental vs. Control.

B: Western-blot analysis was performed to confirm protein up-regulation of MMP-2, e-NOS, uPA, KDR (also called VEGFR2) and to establish the kinetics of induction. A representative experiment is shown for each protein.

C: Quantification of 3-5 experiments described in B. *, , *: P<0.05, P<0.01, P<0,001, experimental vs. Control.

FIG. 4: Effect of Local Injection of Recombinant Human Soluble CD146 in a Rat Ischemic Hind Limb Model A: Rats underwent surgery to induce ischemia in the hind limb. The following day, rats were subjected to a daily local injection of solution containing either 10 µg/ml of c-myc peptide or 10 µg/ml of rh-sCD 146 for 5 or 12 days. Animals were analyzed every 5 days for 20 days after surgery for auto-amputation level and blood perfusion rate (laser-doppler analysis). Results are mean values of 9 different animals in each group. *: P<0.05, experimental vs. Control.

B: Histochemical examination was performed on hind limb muscle sections from control non-treated, c-myc peptide-treated or rh-sCD146-treated rats 12 days after surgery.

C: Estimation of the effects observed by histochemical examination in control animals, c-myc treated and rh-sCD146 treated rats (12 days) on inflammation and fibrosis levels, amount of necrosed fibers, angiogenesis and muscle aspect. Semi-quantifications defined as—(absence), +/−(low expression),+(intermediate expression),++(high expression) are given.

D: Co-immunostainings were performed with anti-CD117 (green) and anti-CD146 (red) antibodies in muscle sections of ischemic rats treated for 2 days with rh-sCD146 or not (Control). Nuclei were labelled with DAPI (blue). The merge pictures are given. Yellow areas correspond to a co-labelling (indicated with an arrow).

FIG. 5: Additive Effect of rh-sCD146 and VEGF on Angiogenic Capacity of Endothelial Progenitor Cells in Vitro A: Proliferation capacity of late EPC was evaluated when rh-sCD 146 (50 ng/ml) and VEGF (20 ng/ml) were added together and compared to the effect of each growth factor added separately. Results are the mean values+/−SEM of 4 different experiments.

B: Migration capacity of late EPC was evaluated using a wound healing assay when rh-sCD146 (50 ng/ml) and VEGF (20 ng/ml) were added together and compared to the effect of each growth factor added separately. Results are the mean values+/−SEM of 4 different experiments.

C: EPC capacity to elaborate pseudo-capillaries in matrigel plugs was evaluated in different conditions. Number of capillary-like structures was evaluated when rh-sCD146 (50 ng/ml) and VEGF (20 ng/ml) were added together and compared to the effect of each growth factor added separately. In addition, the effect of an anti-VEGFR2 antibody (Ab) preincubated before growth factor(s) addition was tested in control condition (Ab), in the presence of rh-sCD146 (Ab+rh-sCD146), in the presence of VEGF (Ab+VEGF) and in the presence of the two growth factors (Ab+rh-sCD146+VEGF). In a last condition, (Washed Ab+rh-sCD146+VEGF), the antibody was preincubated, then washed before addition of the two growth factors. Number of tubes was counted after 5 hours of incubation. Results are the mean values+/−SEM of 6 different experiments. : P<0.01, *: P<0.001, experimental vs. Control.

Figure 6A:
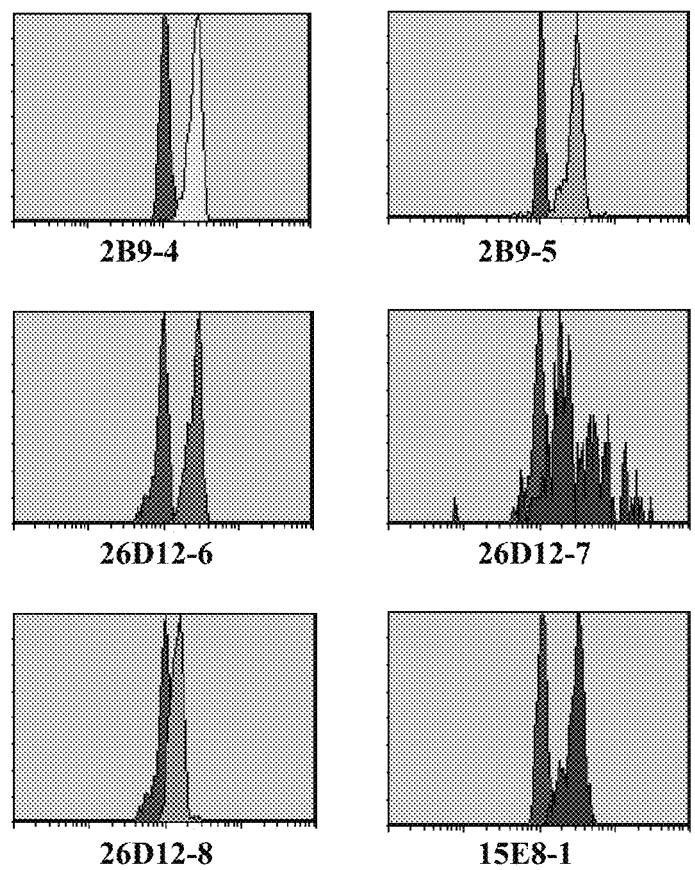
Figure 6B:
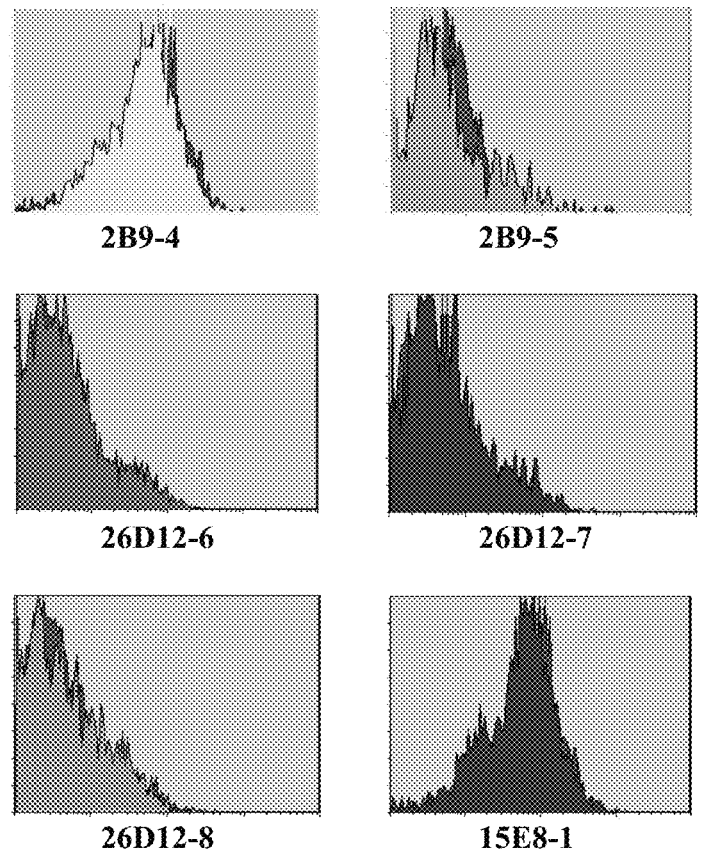

FIG. 6: Characterization of Anti-sCD146 Antibodies.

Antibodies were tested for their ability to bind soluble CD146 (A) but not membrane CD146 (B) by flow cytometry analysis on sCD146 coupled to protein G beads and Huvec, respectively. 6 different antibodies displaying a binding on sCD146 but not on membrane CD146 are shown. ***: p<0.001; $, $$: p<0.01, p<0.001, Ab+sCD146 vs sCD146.

Figure 7:
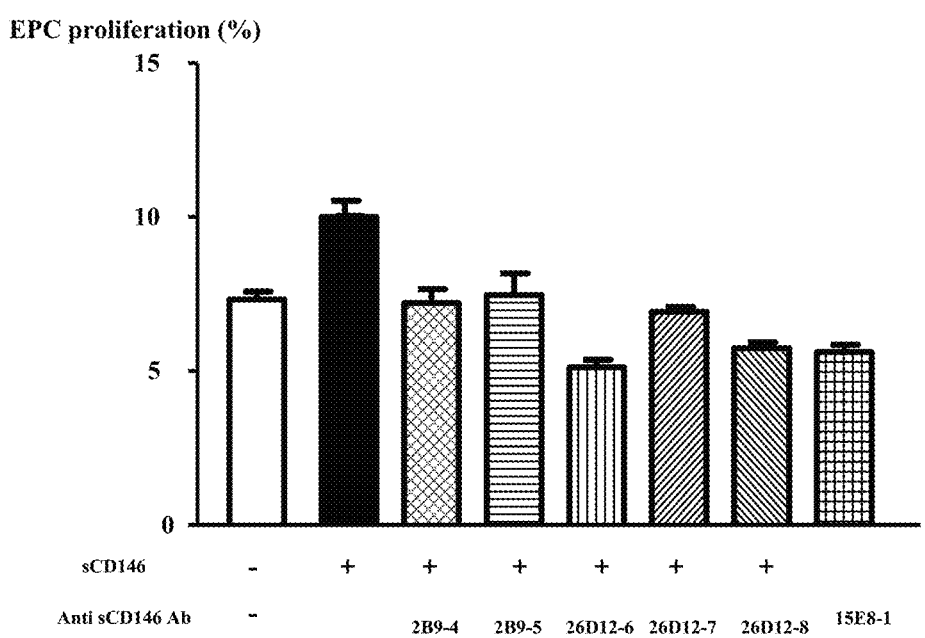

FIG. 7: Blocking Effect of Anti-sCD146 Antibodies on the sCD146-induced Increase in EPC Proliferation.

Antibodies able to bind soluble CD146 but not membrane CD146 were tested for their capacity to inhibit sCD146 effect on EPC proliferation. Among these antibodies, 6 antibodies significantly blocked the sCD146-induced EPC proliferation. ***: p<0.001; $, $$: p<0.01, p<0.001, Ab+sCD146 vs sCD146.

Figure 8:
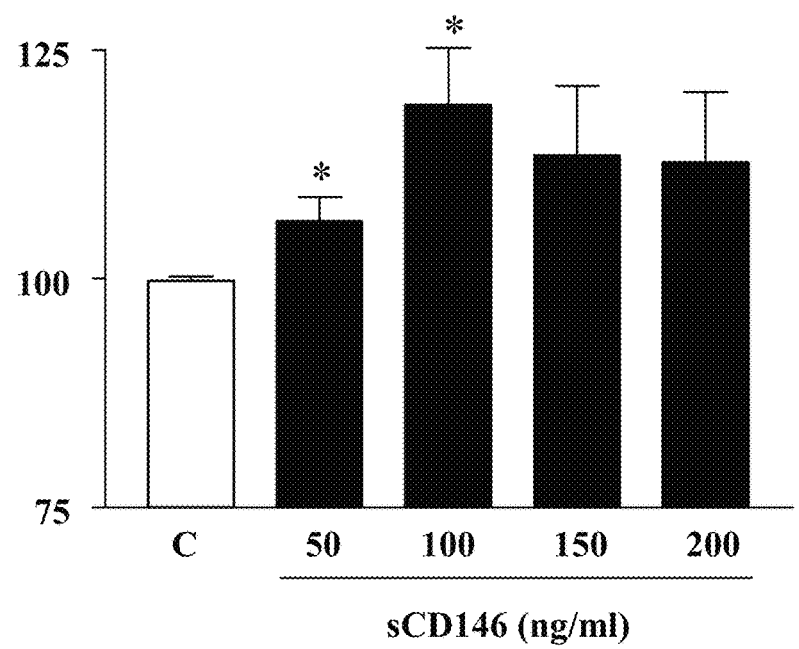

FIG. 8: Effect of Recombinant Human Soluble CD146 on Proliferation of Human Keratinocytes:

The effect of different concentrations of soluble CD146 was tested on the proliferation capacity of human keratinocytes. Results are the mean values+/−SEM of 4 different experiments. *: P<0.05, experimental vs. control (C).

DETAILED DESCRIPTION OF THE INVENTION

In the below description of the invention, the following terms will be employed and are intended to be defined as indicated below.

"Human long CD146 protein" or "long CD146" refers to a human protein, peptide or amino acid molecule, mainly present in the membrane of endothelial cells and having an amino acid sequence corresponding to the following SEQ ID NO: 8:

MGLPRLVCAFLLAACCCCPRVAGVPGEAEQPAPELVEVEVGSTALLKCGL

SQSQGNLSHVDWFSVHKEKRTLIFRVRQGQGQSEPGEYEQRLSLQDRGAT

LALTQVTPQDERIFLCQGKRPRSQEYRIQLRVYKAPEEPNIQVNPLGIPV

NSKEPEEVATCVGRNGYPIPQVIWYKNGRPLKEEKNRVHIQSSQTVESSG

LYTLQSILKAQLVKEDKDAQFYCELNYRLPSGNHMKESREVTVPVFYPTE

KVWLEVEPVGMLKEGDRVEIRCLADGNPPPHFSISKQNPSTREAEEETTN

DNGVLVLEPARKEHSGRYECQAWNLDTMISLLSEPQELLVNYVSDVRVSP

AAPERQEGSSLTLTCEAESSQDLEFQWLREETDQVLERGPVLQLHDLKRE

AGGGYRCVASVPSIPGLNRTQLVKLAIFGPPWMAFKERKVWVKENMVLNL

SCEASGHPRPTISWNVNGTASEQDQDPQRVLSTLNVLVTPELLETGVECT

ASNDLGKNTSILFLELVNLTTLTPDSNTTTGLSTSTASPHTRANSTSTER

KLPEPESRGVVIVAVIVCILVLAVLGAVLYFLYKKGKLPCRRSGKQEITL

PPSRKTELVVEVKSDKLPEEMGLLQGSSGDKRAPGDQGEKYIDLRH

"Human short CD146 protein" or "short CD146" refers to a human protein, peptide or amino acid molecule mainly present in the membrane of endothelial cells and having an amino acid sequence corresponding to the following SEQ ID NO: 9:

MGLPRLVCAFLLAACCCCPRVAGVPGEAEQPAPELVEVEVGSTALLKCGL

SQSQGNLSHVDWFSVHKEKRTLIFRVRQGQGQSEPGEYEQRLSLQDRGAT

LALTQVTPQDERIFLCQGKRPRSQEYRIQLRVYKAPEEPNIQVNPLGIPV

NSKEPEEVATCVGRNGYPIPQVIWYKNGRPLKEEKNRVHIQSSQTVESSG

LYTLQSILKAQLVKEDKDAQFYCELNYRLPSGNHMKESREVTVPVFYPTE

KVWLEVEPVGMLKEGDRVEIRCLADGNPPPHFSISKQNPSTREAEEETTN

DNGVLVLEPARKEHSGRYECQAWNLDTMISLLSEPQELLVNYVSDVRVSP

AAPERQEGSSLTLTCEAESSQDLEFQWLREETDQVLERGPVLQLHDLKRE

AGGGYRCVASVPSIPGLNRTQLVKLAIFGPPWMAFKERKVWVKENMVLNL

SCEASGHPRPTISWNVNGTASEQDQDPQRVLSTLNVLVTPELLETGVECT

ASNDLGKNTSILFLELVNLTTLTPDSNTTTGLSTSTASPHTRANSTSTER

KLPEPESRGVVIVAVIVCILVLAVLGAVLYFLYKKGKLPCRRSGKQEMER

NTSI

"Human soluble CD146 protein" or "soluble CD146" refers to a human protein, peptide or amino acid molecule containing about 552 to about 558 amino acids, preferably 558 amino acids, even more preferably 557, 556, 555, 554, 553 or 552 amino acids.

An example of a human soluble CD146 protein according to the present invention comprises at least residues 1 to 552 inclusive, preferably at least residues 1 to 557 inclusive, of the amino acid sequence SEQ ID NO: 8.

In a particular embodiment, the invention provides a protein comprising an amino acid sequence consisting in SEQ ID NO: 1: MGLPRLVCAFLLAAC-CCCPRVAGVPGEAEQPAPELVEVEVG-STALLKCGLSQSQGNLS HVDWFSVHKEKRTLI-FRVRQGQGQSEPGEYEQRLSLQDRGATLALTQVTP-QDERIFLC QGKRPRSQEYRIQLRVYKAPEEPNIQVN-PLGIPVNSKEPEEVATCVGRNGYPIPQVIWYK NGR-PLKEEKNRVHIQSSQTVESSGLYTLQSILKAQLVKED-KDAQFYCELNYRLPSGNH MKESREVTVPVFYPTEKVWLEVEPVGMLKEG-DRVEIRCLADGNPPPHFSISKQNPSTRE AEEETTNDNGVLVLEPARKEHSGRYECQAWNLDT-MISLLSEPQELLVNYVSDVRVSPA APERQEGSSLTLT-CEAESSQDLEFQWLREETDQVLERGPVLQLH-DLKREAGGGYRCVA SVPSIPGLNRTQLVKLAIFGPPWMAFKERKVWVKEN-MVLNLSCEASGHPRPTISWNVN GTASEQDQDPQRV-LSTLNVLVTPELLETGVECTASNDLGKNTSIL-FLELVNLTTLTPDSN TTTGLSTSTASPHTRANSTSTERKL, which corresponds to a preferred human soluble CD146 protein usable in the context of a mammal treatment, in particular a human treatment, as herein described.

Another human soluble CD146 protein usable in the context of a mammal treatment has an amino acid sequence consisting in one of the below identified sequences:

SEQ ID NO: 2:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQLHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLP

SEQ ID NO: 3:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

-continued

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLPE

SEQ ID NO: 4:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLPEP

SEQ ID NO: 5:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLPEPE

SEQ ID NO: 6:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLPEPES

SEQ ID NO: 7:
MGLPRLVCAFLLAACCCCPRVAGVPGEAEQPAPELVEVEVGSTALLKCGLSQSQGNLS

HVDWFSVHKEKRTLIFRVRQGQGQSEPGEYEQRLSLQDRGATLALTQVTPQDERIFLC

```
-continued
QGKRPRSQEYRIQLRVYKAPEEPNIQVNPLGIPVNSKEPEEVATCVGRNGYPIPQVIWYK

NGRPLKEEKNRVHIQSSQTVESSGLYTLQSILKAQLVKEDKDAQFYCELNYRLPSGNH

MKESREVTVPVFYPTEKVWLEVEPVGMLKEGDRVEIRCLADGNPPPHFSISKQNPSTRE

AEEETTNDNGVLVLEPARKEHSGRYECQAWNLDTMISLLSEPQELLVNYVSDVRVSPA

APERQEGSSLTLTCEAESSQDLEFQWLREETDQVLERGPVLQLHDLKREAGGGYRCVA

SVPSIPGLNRTQLVKLAIFGPPWMAFKERKVWVKENMVLNLSCEASGHPRPTISWNVN

GTASEQDQDPQRVLSTLNVLVTPELLETGVECTASNDLGKNTSILFLELVNLTTLTPDSN

TTTGLSTSTASPHTRANSTSTERKLPEPESR
```

Among the previous sequences, SEQ ID NO: 1 and SEQ ID NO: 6 are particularly preferred. The soluble CD146 is present in the human serum and extracted therefrom or artificially reproduced. In a preferred embodiment, the soluble CD146 contains the amino acid sequence consisting in SEQ ID NO: 1 or SEQ ID NO: 6. Preferably, the herein disclosed human soluble CD146 is a biologically active human soluble CD146, i.e., it initiates, promotes, increases or stimulates vasculogenesis and/or angiogenesis in vitro, ex vivo or in vivo. Preferably the soluble CD146 displays a chemotactic activity, i.e., the soluble CD146 is able to induce mobilization or migration of endogeneous or exogeneous cells to the site wherein vasculogenesis and/or angiogenesis is to occurred, preferably cells of endothelial origin (KDR+ and/or CD31+ cells), preferably selected from immature endothelial cells (in particular CD117+ cells), mature endothelial cells (in particular KDR+ cells), endothelial progenitor cells (EPC), such as stem cell (typically bone-marrow derived stem cells), and mixtures thereof, and/or allows or favors the organization of such cells into vascular-like structures. A biologically active human soluble CD146 is also able to activate endothelial cells as defined previously, i.e., to increase their ability to proliferate and/or promote pseudo-capillaries genesis.

The herein disclosed human soluble CD146 is further preferably capable of interacting with the short isoform of CD146 ("short CD 146"), a receptor of CD146, in particular a receptor of soluble CD146, and/or to a complex comprising such a short isoform of CD146 and receptor of soluble CD146, on a cell preferably selected from the above identified cells.

A typical human soluble CD146 protein according to the present invention is, as explained previously, a protein usable in the context of a treatment (a therapeutic or prophylactic protein) or in the context of diagnostic, and compatible with an administration to a human, in particular by way of injection in the bloodstream, and/or by way of subcutaneous and/or intramuscular administration.

The term "Treatment" refers to both therapeutic and prophylactic or preventive treatment or measures able to alleviate or cure a disease, disorder or dysfunctional state. Such a treatment is intended for a mammal subject, preferably a human subject in need thereof. Are considered as such, the subjects suffering from a disease, disorder or dysfunctional state leading to tissue ischemia, or those considered "at risk of developing" such a disease, disorder or dysfunctional state, in which this has to be prevented.

Disease, disorder or dysfunctional state leading to tissue ischemia are disease, disorder or dysfunctional state leading to abnormal vasculogenesis and/or angiogenesis, in particular disease, disorder or dysfunctional state leading to an undesirable excessive neovascularization, vascular permeability (alteration of the intercellular junctions of endothelial cells) and/or vascular endothelial cell growth. Examples of such disease include cancer; diabetes; age-related macular degeneration; rheumatoid arthritis; psoriasis; any known vascular diseases including atherosclerotic vascular disease, cardiovascular disease such as coronary artery disease, ischemic heart disease and stroke, cerebrovascular ischemia, peripheral vascular disease such as peripheral artery occlusive disease.

In these conditions leading to an undesirable neovascularization, new blood vessels feed diseased tissues, destroy normal tissues, and in the case of cancer, the new vessels allow tumor cells to escape into the circulation and lodge in other organs (tumor metastases).

Disorders may be the consequence of a disease as described above or of a trauma. Typical disorders are for example inflammation, oedema, fibrosis or necrosis.

Examples of dysfunctional states are characterized by a lack of or, on the contrary, an excessive expression of at least one particular form of CD146 or of a receptor for CD146, in particular for soluble CD146, compared to a standard expression. Other Examples of dysfunctional states are characterized by a decreased or excessive expression of a gene selected from the gene encoding e-NOS, uPa, MMP-2 and KDR, compared to a standard expression.

Dysfunctional states characterized by a lack of expression are advantageously treated by a human soluble CD146, or a therapeutic composition comprising such a soluble CD146, or a cell (as described below) according to the present invention.

Dysfunctional states characterized by an excessive expression, such as cancer, are advantageously treated by an antibody directed against a human soluble CD146, or any other antagonist directed against such a human soluble CD146, as herein described. In a particular embodiment, a dysfunctional state such as a cancer, may be treated by an antibody directed against a human soluble CD146 together with an antibody directed against an angiogenic factor such as VEGF.

The present description therefore identifies an isolated human soluble CD146 protein containing about 552 to 558 amino acids, preferably 552 to 557 amino acids, even more preferably 552 or 557 amino acids. "Isolated" means identified and separated or recovered from a component of its natural source or environment in a human subject, in particular from bone marrow or blood of said subject.

A preferred human soluble CD146 protein comprises an amino acid sequence consisting in SEQ ID NO: 1 or SEQ ID NO: 6, and corresponds to a protein usable in the context of a mammal treatment, in particular a human treatment, as herein described.

The present description further provides nucleic acid molecules which respectively encode the proteins of the invention herein described.

Such nucleic acid molecules are RNA or DNA that preferably each encode a biologically active human CD146, in particular a human soluble CD146 of the invention, the human short form of CD146, and recombinant forms thereof.

Examples of nucleic acid sequences are provided below:

SEQ ID NO: 17
(short CD146)
```
ATGGGGCTTCCCAGGCTGGTCTGCGCCTTCTTGCTCGCCGCCTGCTGCTGCTGTCCTC
GCGTCGCGGGTGTGCCCGGAGAGGCTGAGCAGCCTGCGCCTGAGCTGGTGGAGGT
GGAAGTGGGCAGCACAGCCCTTCTGAAGTGCGGCCTCTCCCAGTCCCAAGGCAACC
TCAGCCATGTCGACTGGTTTTCTGTCCACAAGGAGAAGCGGACGCTCATCTTCCGTG
TGCGCCAGGGCCAGGGCCAGAGCGAACCTGGGGAGTACGAGCAGCGGCTCAGCCT
CCAGGACAGAGGGGCTACTCTGGCCCTGACTCAAGTCACCCCCCAAGACGAGCGCA
TCTTCTTGTGCCAGGGCAAGCGCCCTCGGTCCCAGGAGTACCGCATCCAGCTCCGC
GTCTACAAAGCTCCGGAGGAGCCAAACATCCAGGTCAACCCCCTGGGCATCCCTGT
GAACAGTAAGGAGCCTGAGGAGGTCGCTACCTGTGTAGGGAGGAACGGGTACCCC
ATTCCTCAAGTCATCTGGTACAAGAATGGCCGGCCTCTGAAGGAGGAGAAGAACCG
GGTCCACATTCAGTCGTCCCAGACTGTGGAGTCGAGTGGTTTGTACACCTTGCAGA
GTATTCTGAAGGCACAGCTGGTTAAAGAAGACAAAGATGCCCAGTTTTACTGTGAG
CTCAACTACCGGCTGCCCAGTGGGAACCACATGAAGGAGTCCAGGGAAGTCACCGT
CCCTGTTTTCTACCCGACAGAAAAGTGTGGCTGGAAGTGGAGCCCGTGGGAATGC
TGAAGGAAGGGGACCGCGTGGAAATCAGGTGTTTGGCTGATGGCAACCCTCCACCA
CACTTCAGCATCAGCAAGCAGAACCCCAGCACCAGGGAGGCAGAGGAAGAGACAA
CCAACGACAACGGGGTCCTGGTGCTGGAGCCTGCCCGGAAGGAACACAGTGGGCG
CTATGAATGTCAGGGCCTGGACTTGGACACCATGATATCGCTGCTGAGTGAACCAC
AGGAACTACTGGTGAACTATGTGTCTGACGTCCGAGTGAGTCCCGCAGCCCCTGAG
AGACAGGAAGGCAGCAGCCTCACCCTGACCTGTGAGGCAGAGAGTAGCCAGGACC
TCGAGTTCCAGTGGCTGAGAGAAGAGACAGGCCAGGTGCTGGAAAGGGGGCCTGT
GCTTCAGTTGCATGACCTGAAACGGGAGGCAGGAGGCGGCTATCGCTGCGTGGCGT
CTGTGCCCAGCATACCCGGCCTGAACCGCACACAGCTGGTCAACGTGGCCATTTTT
GGCCCCCCTTGGATGGCATTCAAGGAGAGGAAGGTGTGGGTGAAAGAGAATATGG
TGTTGAATCTGTCTTGTGAAGCGTCAGGGCACCCCCGGCCCACCATCTCCTGGAAC
GTCAACGGCACGGCAAGTGAACAAGACCAAGATCCACAGCGAGTCCTGAGCACCC
TGAATGTCCTCGTGACCCCGGAGCTGTTGGAGACAGGTGTTGAATGCACGGCCTCC
AACGACCTGGGCAAAAACACCAGCATCCTCTTCCTGGAGCTGGTCAATTTAACCAC
CCTCACACCAGACTCCAACACAACCACTGGCCTCAGCACTTCCACTGCCAGTCCTC
ATACCAGAGCCAACAGCACCTCCACAGAGAGAAAGCTGCCGGAGCCGGAGAGCCG
GGGCGTGGTCATCGTGGCTGTGATTGTGTGCATCCTGGTCCTGGCGGTGCTGGGCGCT
GTCCTCTATTTCCTCTATAAGAAGGGCAAGCTGCCGTGCAGGAGCTCAGGGAAGCAG
GAGATGGAGAGAAATACATCGATCTGA
```

SEQ ID NO: 10
(soluble CD146)
```
ATGGGGCTTCCCAGGCTGGTCTGCGCCTTCTTGCTCGCCGCCTGCTGCTGCTGTCCTC
GCGTCGCGGGTGTGCCCGGAGAGGCTGAGCAGCCTGCGCCTGAGCTGGTGGAGGT
```

-continued

```
GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTG
```

SEQ ID NO: 11
(soluble CD146)
```
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG
```

-continued

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCG

SEQ ID NO: 12
(soluble CD146)
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

```
                                                   -continued
GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCGGAG

SEQ ID NO: 13
(soluble CD146)
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCGGAGCCG
```

-continued

SEQ ID NO: 14
(soluble CD146)
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCGGAGCCGGAG

SEQ ID NO: 15
(soluble CD146)
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

-continued

```
ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC

AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCGGAGCCGGAGAGC

SEQ ID NO: 16
(soluble CD146)
ATGGGGCTTCCCAGGCTGGTCTGCGCCTTCTTGCTCGCCGCCTGCTGCTGCTGTCCTC

GCGTCGCGGGTGTGCCCGGAGAGGCTGAGCAGCCTGCGCCTGAGCTGGTGGAGGT

GGAAGTGGGCAGCACAGCCCTTCTGAAGTGCGGCCTCTCCCAGTCCCAAGGCAACC

TCAGCCATGTCGACTGGTTTTCTGTCCACAAGGAGAAGCGGACGCTCATCTTCCGTG

TGCGCCAGGGCCAGGGCCAGAGCGAACCTGGGGAGTACGAGCAGCGGCTCAGCCT

CCAGGACAGAGGGGCTACTCTGGCCCTGACTCAAGTCACCCCCCAAGACGAGCGCA

TCTTCTTGTGCCAGGGCAAGCGCCCTCGGTCCCAGGAGTACCGCATCCAGCTCCGC

GTCTACAAAGCTCCGGAGGAGCCAAACATCCAGGTCAACCCCCTGGGCATCCCTGT

GAACAGTAAGGAGCCTGAGGAGGTCGCTACCTGTGTAGGGAGGAACGGGTACCCC

ATTCCTCAAGTCATCTGGTACAAGAATGGCCGGCCTCTGAAGGAGGAGAAGAACCG

GGTCCACATTCAGTCGTCCCAGACTGTGGAGTCGAGTGGTTTGTACACCTTGCAGA

GTATTCTGAAGGCACAGCTGGTTAAAGAAGACAAAGATGCCCAGTTTTACTGTGAG

CTCAACTACCGGCTGCCCAGTGGGAACCACATGAAGGAGTCCAGGGAAGTCACCGT

CCCTGTTTTCTACCCGACAGAAAAAGTGTGGCTGGAAGTGGAGCCCGTGGGAATGC

TGAAGGAAGGGGACCGCGTGGAAATCAGGTGTTTGGCTGATGGCAACCCTCCACCA

CACTTCAGCATCAGCAAGCAGAACCCCAGCACCAGGGAGGCAGAGGAAGAGACAA

CCAACGACAACGGGGTCCTGGTGCTGGAGCCTGCCCGGAAGGAACACAGTGGGCG

CTATGAATGTCAGGGCCTGGACTTGGACACCATGATATCGCTGCTGAGTGAACCAC
```

```
-continued
AGGAACTACTGGTGAACTATGTGTCTGACGTCCGAGTGAGTCCCGCAGCCCCTGAG

AGACAGGAAGGCAGCAGCCTCACCCTGACCTGTGAGGCAGAGAGTAGCCAGGACC

TCGAGTTCCAGTGGCTGAGAGAAGAGACAGGCCAGGTGCTGGAAAGGGGCCTGT

GCTTCAGTTGCATGACCTGAAACGGGAGGCAGGAGGCGGCTATCGCTGCGTGGCGT

CTGTGCCCAGCATACCCGGCCTGAACCGCACACAGCTGGTCAACGTGGCCATTTTT

GGCCCCCCTTGGATGGCATTCAAGGAGAGGAAGGTGTGGGTGAAAGAGAATATGG

TGTTGAATCTGTCTTGTGAAGCGTCAGGGCACCCCCGGCCCACCATCTCCTGGAAC

GTCAACGGCACGGCAAGTGAACAAGACCAAGATCCACAGCGAGTCCTGAGCACCC

TGAATGTCCTCGTGACCCCGGAGCTGTTGGAGACAGGTGTTGAATGCACGGCCTCC

AACGACCTGGGCAAAAACACCAGCATCCTCTTCCTGGAGCTGGTCAATTTAACCAC

CCTCACACCAGACTCCAACACAACCACTGGCCTCAGCACTTCCACTGCCAGTCCTC

ATACCAGAGCCAACAGCACCTCCACAGAGAGAAAGCTGCCGGAGCCGGAGAGCCG

G
```

The natural (non recombinant) molecules may be isolated, for example from a nucleic acid library prepared from a tissue known to express the desired protein, e.g., blood, in particular serum or bone marrow, the library being screened with an appropriate probe, or from a tissue sample (bone marrow, blood, serum, etc.), preferably a sample of the subject to be treated (see for example Hoskins R A, Stapleton M, George R A, Yu C, Wan K H, Carlson J W, Celniker S E. Rapid and efficient cDNA library screening by self-ligation of inverse PCR products (SLIP). Nucleic Acids Research 2005; 33:185-197).

The nucleic acid molecules may otherwise be artificially produced, for example by oligonucleotides synthesis (see for example Michaels M L, Hsiao H M, Miller J H. Using PCR to extend the limit of oligonucleotide synthesis. Biotechniques. 1992; 12:44- 48).

A preferred human soluble CD146 protein according to the present invention may be obtained using a method comprising the following steps of transfecting a mammalian cell with an appropriate vector expressing a human soluble CD146 protein and isolating the expressed human CD 146 protein.

Herein described is a recombinant human soluble CD146 (rh-sCD146) protein fused to another polypeptide, such as a tag polypeptide sequence (see the c-myc tagged human soluble CD 146 in the experimental part wherein the sequence of the soluble CD146 is SEQ ID NO: 7).

The nucleic acid molecule can be provided in a replicable vector comprising the nucleic acid molecule operably linked to control sequences recognized by a host cell transfected or transformed with the vector, in particular a mature or immature endothelial cell or a progenitor cell, preferably an endothelial progenitor cell (EPC, also herein identified as EPDC), typically a cell as previously herein described. The invention further provides such an host cell comprising the vector or the nucleic acid molecule as further explained below.

The amino acid molecules of the present invention can be designed to be compatible with a diagnostic, therapeutic or prophylactic use in a mammal, preferably a human. They can be, for example, glycosylated, methylated, acetylated, phosphorylated, for targeting different types of tissues, in particular a pathological tissue such as, typically, an ischemic tissue, preferably in a human.

Suitable host cells for the expression of glycosylated soluble human CD146 may be selected from mammalian cell lines, for example CHO cells.

In another embodiment, the invention provides a composition, in particular a pharmaceutical composition useful for promotion of vascular cell growth, typically endothelial cell growth, comprising, preferably in a therapeutically effective amount, a soluble CD146 protein, as herein described, in a pharmaceutically acceptable carrier or excipient.

A "therapeutically affective amount" of a soluble CD146 protein is an amount allowing the treatment, as previously defined, of a mammal.

A pharmaceutically acceptable excipient, vehicle or carrier, usable in the context of the present invention, is for example a saline, isotonic, buffered solution such as Mannitol 20%, optionally combined with stabilizing agents such as isogenic albumin or any other stabilizing protein, glycerol, etc., and also adjuvants such as polybrene or DEAE dextrans, etc.

In a particular aspect, the herein described compositions comprising a soluble CD46, preferably a human soluble CD146 may further comprise at least one other angiogenic factor.

In the context of the present invention an angiogenic factor is a factor which favors blood vessel development.

Angiogenic factors usable in the context of the present invention may be selected from angiogenin, angiopoietin-1, Del-1, fibroblast growth factors: acidic (aFGF) and basic (bFGF), follistatin, granulocyte colony-stimulating factor (G-CSF), granulocyte-macrophage colony stimulating factor (GM-CSF), stem cell factor (SCF), hepatocyte growth factor (HGF)/scatter factor (SF), interleukin-8 (IL-8), leptin, midkine, placental growth factor, platelet-derived endothelial cell growth factor (PD-ECGF), platelet-derived growth factor-BB (PDGF-BB), pleiotrophin (PTN), erytropoietin (EPO), endothelial nitric oxyd synthase (e-NOS), progranulin, proliferin, transforming growth factor-alpha (TGF-alpha), transforming growth factor-beta (TGF-beta), tumor necrosis factor-alpha (TNF-alpha), vascular endothelial growth factor (VEGF), vascular permeability factor (VPF), Angiopoietin-1 (Ang1), plasminogen activator urokinase (PLAU/u-Pa), the matrix metallopeptidase MMP-2, the VEGF receptor 2 (KDR), stromal-cell-derived-factor-1 (SDF-1), etc., and a mixture thereof.

Preferred angiogenic factors may be selected from vascular endothelial growth factor (VEGF—see experimental section and FIG. 5), stromal-cell-derived-factor-1 (SDF-1), basic fibroblast growth factors (bFGF), erytropoietin (EPO), granulocyte colony-stimulating factor (G-CSF), granulocyte-macrophage colony stimulating factor (GM-CSF), stem cell factor (SCF), interleukin-8 (IL-8) and a mixture thereof.

In another particular aspect, the herein described compositions comprising an antibody directed against a soluble CD146 may further comprise at least one other antibody directed against one of the previously identified angiogenic factor.

In another particular aspect, the herein described compositions comprising a human soluble CD146 may in addition comprise a mature or immature endothelial cell or a progenitor cell, typically of human origin, preferably in vitro-expanded progenitor cells, in particular stem cells or endothelial progenitor cells, typically cells derived from blood or bone marrow, for example selected from cells expressing CD34, CD133, CD31, VE-cadherin, VEGFR2, c-Kit, CD45 and/or Tie-2.

Compositions comprising cells as previously mentioned contacted with a soluble CD146 as herein defined before being optionally incorporated in a pharmaceutically acceptable excipient are an embodiment of the present invention as further explained below. Such compositions do not comprise added soluble CD 146.

In a preferred embodiment, the progenitor cell is a recombinant progenitor cell. Such a recombinant cell may be genetically modified using an appropriate vector comprising or consisting in a genetic or nucleic acid construct expressing, preferably enabling an overexpression of, a particular biologically active form of CD146, preferably of the human short form of CD146 or human soluble form of CD146, as defined previously.

Many vectors are available. Preferred vectors may be selected from a plasmid, a retrovirus, a lentivirus and an adenovirus. The vector components generally include, but are not limited to, one or more of the following: a signal sequence, an origin of replication, one or more marker genes, an enhancer element, a promoter, and a transcription termination sequence, easily selectable by the man of the art (see for example Liu J W, Pernod G, Dunoyer-Geindre S, Fish R J, Yang H, Bounameaux H, Kruithof E K. Promoter dependence of transgene expression by lentivirus-transduced human blood-derived endothelial progenitor cells. Stem Cells. 2006; 24:199-208).

Such a progenitor cell may be transfected with the appropriate vector, preferably with a plasmid as described previously, according to known protocols, preferably a protocol appropriate to endothelial progenitor cells such as electroporation or use of liposomes, and then cultured in any known suitable media (a medium comprising EGM-2 for example), optionally supplemented with one or more of the following: an appropriate hormone, growth factor, buffer, etc. The progenitor cells may then be expanded in vitro using any method known by the man of the art (see for example Delorme B et al. Presence of endothelial progenitor cells, distinct from mature endothelial cells, within human CD146+ blood cells. Thromb Haemost. 2005 ;94:1270-9).

Also incorporated in the present invention is the use of a human soluble CD146 protein according to the invention to prepare, ex vivo, a mature or immature endothelial cell or a progenitor cell, as previously defined, exhibiting therapeutic or prophylactic properties, in particular capable of stimulating angiogenesis in a human body. Inventors have indeed discovered that such cells contacted, "pre-treated" or "primed" with a human soluble CD146 protein according to the invention are able by themselves, once administered to a subject, to induce or stimulate vasculogenesis and/or angiogenesis. The "pre-treated" or "primed" cells have been contacted with, or cultured in the presence of, a human soluble CD146 protein according to the invention before being optionally incorporated into a pharmaceutically acceptable support.

Such cells are further object of the present invention as well as the pharmaceutical compositions comprising said cells, preferably in a pharmaceutically acceptable support. While preparing such pharmaceutical compositions further adding human soluble CD146 is optional.

Preferred "pre-treated" or "primed" cells are cells which have been genetically modified, as explained previously, to overexpress the short form of CD146 or soluble CD146.

In a further aspect, the invention relates to a protein or a composition as herein described for use in the treatment of a disease, disorder or dysfunctional state leading to tissue ischemia or characterized by a decreased activation of a receptor for CD146, in particular soluble CD146, or by a decreased expression of a gene selected from the gene encoding e-NOS, uPa, MMP-2 and KDR, compared to standard values.

The invention relates to a protein or a composition as herein described for use in the prevention of ischemia.

In particular, the invention relates to the use of a protein or a composition as herein described to prepare a composition for preventing or treating a disease, a disorder or a dysfunctional state as herein previously identified.

In another particular embodiment, the invention provides a method of preventing or treating a disease, a disorder or a dysfunctional state in a mammal, preferably a human, as herein identified, in particular a method of preventing or treating a tissue ischemia, comprising administering to the mammal, an effective amount of a composition, as herein described, comprising a soluble CD146 protein.

In a further aspect, the invention relates to the use of a protein or a composition as herein described to improve the aesthetic appearance of a scar or, in prevention, to facilitate the cicatrization or healing of a wound, a cut or an incision.

An object of the present invention is a protein or a composition as herein described for use in the cicatrization of a mammal epithelium, in particular a human epithelium, in particular following a wound, a cut or an incision, or in the context of a skin graft.

Another object of the present invention is a protein or a composition as herein described for use in the prevention or treatment of an eschar or a bedsore in a mammal, in particular a human.

Preferred compositions for use in the context of cicatrisation will be advantageously formulated for topic application according to methods known by the man of the art.

In another embodiment, the present invention further provide a monoclonal antibody which selectively binds to a human soluble CD146 protein according to the present invention, preferably to the protein comprising an amino acid sequence consisting in SEQ ID NO: 1 or SEQ NO: 6.

This antibody preferably also neutralizes a biological activity of the human soluble CD146 protein of the invention. Preferably, the monoclonal antibody decreases or inhibits neovascularization, vascular permeability and/or vascular endothelial cell growth in a subject as herein defined, typically a mammal, preferably a human.

The monoclonal antibody is also preferably able to reduce or suppress an excessive expression (compared to a standard expression) of a soluble CD146 receptor, or an excessive expression (compared to a standard expression) of a gene selected from the gene encoding e-NOS, uPa, MMP-2 and KDR.

Antibodies binding both the human soluble CD146 protein and a CD146 or soluble CD146 protein receptor (or a CD146 protein receptor subunit) are also within the scope of the present invention. Methods of making such antibodies are known in the art (See for example Despoix N, Walzer T, Jouve N, Blot-Chabaud M, Bardin N, Paul P, Lyonnet L, Vivier E, Dignat-George F, Vély F. Mouse CD146/MCAM is a marker of natural killer cell maturation. Eur J Immunol. 2008;38: 2855-64).

Preferred antibodies selected by inventors in the context of the present invention, capable of selectively binding soluble CD146 (versus membrane CD146), are identified on FIG. 7 (2B9-4, 2B9-5, 26D12-6, 26D12-7, 26D12-8 and 15E8-1).

The herein described antibodies may be incorporated into a composition further comprising a pharmaceutically acceptable carrier, in respective appropriate dosages.

In a particular aspect, the herein described compositions comprising an antibody as herein described, in particular an antibody specifically directed against the human soluble CD146 herein described which preferably consists in SEQ ID NO: 1 or SEQ ID NO: 6, may further comprise at least one other anti-angiogenic factor. In the context of the present invention an anti-angiogenic factor is a factor which inhibits or interferes with blood vessel development. Anti-angiogenic factors usable in the context of the present invention may be selected from an antibody directed against an angiogenic factor as previously defined, angioarrestin, angiostatin (plasminogen fragment), antiangiogenic antithrombin III, cartilage-derived inhibitor (CDT), CD59 complement fragment, endostatin (collagen XVIII fragment), fibronectin fragment, gro-beta, an heparinase, heparin hexasaccharide fragment, human chorionic gonadotropin (hCG), interferon alpha/beta/gamma, Interferon inducible protein (IP-10), interleukin-12, kringle 5 (plasminogen fragment), metalloproteinase inhibitors (TIMPs), 2-Methoxyestradiol, placental ribonuclease inhibitor, plasminogen activator inhibitor, platelet factor-4 (PF4), prolactin 16kD fragment, proliferin-related protein (PRP), a retinoid, tetrahydrocortisol-S, thrombospondin-1 (TSP-1), transforming growth factor-beta (TGF-b), vasculostatin, vasostatin (calreticulin fragment), etc., and a mixture thereof.

The antibody, or a pharmaceutical composition comprising at least said antibody and a pharmaceutically acceptable carrier, herein disclosed, can be used in a mammal, preferably a human, for preventing or treating a disease, disorder or dysfunctional state characterized by an undesirable excessive neovascularization or vascular permeability, such as a cancer, in particular a breast cancer or a melanoma, or by an overexpression or excessive activation of a receptor for CD146, in particular soluble CD146, or by an excessive expression of a gene selected from the gene encoding e-NOS, uPa, MMP-2 and KDR, compared to standard expressions.

The doses of the diagnostic or pharmaceutical composition may be adjusted by the skilled person depending on the treated subject, the route of administration, the targeted tissue, the biologically active compound (as herein disclosed), etc.

Various protocols may be used for the administration, such as simultaneous or sequential administration of the human soluble CD146 and of any other compound as defined previously ("pre-treated", "primed", and/or genetically modified cells as described previously for example), single or repeated administration, etc., which may be adjusted by the skilled person.

The pharmaceutical composition containing the product according to the invention may be administered to a patient for example systemically, subcutaneously, intraspinally or intracerebrally, given the targeted pathological tissue or area. Preferred modes of injection are systemical injections, in particular intra-venous or intra-arterial injections, or subcutaneous injections.

The molecules of the present invention may further be used in methods of diagnostic. The term diagnostic designates any in vivo, ex vivo or in vitro diagnosis, including molecule detection, monitoring, quantification, comparison, etc. In particular, the human soluble CD146 protein may be used as a biomarker providing an indication of the presence of a disease in a mammal, preferably a human, in particular an ischemia or a cancer, of metastasis of a tumor, or of the evolution of such a diseased state. In particular the serum concentration of the human soluble CD146 protein may be an indication of high value in this regards. The measured value may be indeed compared to standard values associated to a healthy status of a subject. An overexpression of the soluble form of CD146 may be, in particular, indicative of the presence of a cancer.

The term diagnosis also includes the use of the molecules to screen compounds or treatments that cause or increase apoptosis of a cell, in vitro, ex vivo or in vivo.

Also herein provided is a kit comprising at least one biologically active product as herein described, such as a human soluble CD146, an antibody, in particular a monoclonal antibody, directed against said human soluble CD146, a "pre-treated" or "primed" (stimulated by said human soluble CD146) and/or genetically modified (to overexpress the short form of CD146 or soluble CD146) cell, and optionally (ii) a leaflet providing guidelines.

Further aspects and advantages of the present invention will be described in the following examples, which should be regarded as illustrative and not limiting. All references cited in the present application are herein incorporated by reference.

EXAMPLES

Example 1

Soluble CD146 Displays Angiogenic Properties and Promotes Neovascularisation in Experimental Hind Limb Ischemia Materials and Methods
Recombinant Human Soluble CD146

A c-myc tagged recombinant protein corresponding to the soluble form of human CD146 was obtained from Biocytex (Marseille, France). Epitope tagging of CD146 at its N-terminus enabled us to detect specifically the recombinant molecule using an anti- c-myc peptide antibody (Abcam) and to distinguish it from endogenous CD146.

Matrigel Plugs in Vivo

Non immunocompromised or nude mice were anesthetized and 400 µl ice-cold matrigel, containing either 0.1 µg/µl c-myc peptide or 0.1 µg/µl rh-sCD146, were injected respectively into the left and right groin area of each animal Animals were then injected or not with 500,000 late EPC depending on the experiment. After 12 days, the matrigel plugs were removed and frozen. Procedures described above were conducted under an institutional approved animal use protocol.

Induction of Hind Limb Ischemia in Rats

Male rats were subjected to unilateral hind limb ischemia by complete resection of the entire left femoral artery followed by microbeads injection. Laser-doppler tissue imaging showed that obstruction of the left common femoral artery decreased blood perfusion by about 90% at day 1. After surgery, animals were split in four treatment groups: two control groups injected daily in ischemic adductor muscles with 10 µg c-myc peptide for either 5 or 12 days; two experimental groups treated as the control groups except that the c-myc peptide was replaced with recombinant human soluble CD146 (rh-sCD146). The procedures described above were conducted under an institutional approved animal use protocol.

Laser Doppler Blood Flow Analysis

The ratio of the ischemic vs. normal hind limb blood flow was measured using a laser Doppler blood flow analyzer. At different time points (postoperative days 1, 5, 10, 15 and 21), animals were subjected to 2 consecutive laser scannings over the regions of interest (leg and feet). Blood flow was expressed as the ischemic vs. normal hind limb ratio.

Morphological, Histological and Immunochemical Assessment.

At day 20 after ischemia induction or initiation, animals were sacrificed with a lethal dose of pentobarbital (Clin Midy, Gentilly, France) and muscles were fixed by transcardiac perfusion with 4% phosphate-buffered paraformaldehyde (Sigma-Aldrich). Frozen sections were cut with a sliding microtome (CM1900, Leica, France SA) and stored at −20° C. All sections were examined by investigators blind to the experimental conditions using a light microscope (Eclipse TE 2000-U, Nikon France SA) equipped with a digital camera (DXM1200, Nikon France SA).

Histological analysis was performed 20 days after ischemia induction by microscopic examination of the cell changes induced in the core and in the boundary zone of the ischemic area, on serial muscle sections stained with eosin-hematoxylin. Sections were examined under light microscope on two consecutive sections. A semi-quantitative evaluation of the cell changes was performed using a four-point scale from absence (−) to intense (++). Capillary density was determined by microscopic analysis of muscle cryosections.

In in vivo matrigel plugs experiments or experiments on muscles, 5 µm-thick sections were used for staining. After blocking in normal serum, the sections were treated overnight at 4° C. with anti-CD31 (1/50), anti-CD117 (1/50), anti-CD34 (1/40), anti-CD45 (1/200) antibody, anti-MOMA2 antibody (1/200), anti-αsma antibody (1/80), anti-CD33 antibody (1/100), or anti-CD146 antibody (1/100). Signal amplification utilized fluorochrome (Alexa 488 or Alexa 647)-conjugated secondary antibodies (1/250; Invitrogen) when non-coupled. Sections were counterstained with DAPI (1:1000, Sigma-Aldrich), rinsed and mounted. For the assessment of non-specific staining, alternating sections were incubated without the primary antibody.

Isolation of Circulating Progenitor Endothelial Cells and Cell Culture

Human umbilical cord blood samples harvested from donors after consent were collected in a heparinized tube. Mononuclear cells (MNC) were isolated by density gradient centrifugation. Cord blood MNC were then pre-plated in RPMI/10% fetal calf serum (FCS) for 24 hours in plastic flasks. Non adherent cells were plated onto 0.2% gelatin-coated 24-well plates ($10^5$ cells per well) and maintained in endothelial basal medium-2 (EBM-2) supplemented with EGM-2 SingleQuots (EGM-2 medium, Clonetics, Walkersville, Md., USA). For expansion of endothelial progenitor derived cells (EPDC), also called late endothelial progenitor cells (EPC), colonies were trypsinized and cells were replated on plates or labtek slides depending on the experiment. Cells were maintained under standard conditions (humidified atmosphere, 5% $CO_2$, 37° C.).

For EPDC stimulation experiments, cells were maintained for 3 hours in EBM2 and then stimulated with 50 ng/ml of recombinant human soluble CD146 (rh-sCD146) (biocytex), 20 ng/ml VEGF (R&D systems, Minneapolis, Minn., USA) or the appropriate solution for 1 to 24 hours, depending on the experiment.

Chemotactic Activity in vitro

Experiments were performed on semi-permeable Transwell filters (8 m porosity; 24 wells; B&D) in EGM2 medium. 500,000 EPDC previously labelled for 30 min at 37° C. with calcein were seeded in the upper compartment. Different concentrations of rh-sCD146 were then added in the lower compartment and migration of EPDC across the filter was measured after an overnight incubation at 37° C. Fluorescence intensity was measured using a cytofluor apparatus (Cytofluor Series 4000; PerSeptive Biosystems).

Endothelial Cell Tube Formation in Matrigel 96-well plates were pre-coated with 1:1 mixture of cold Matrigel™ Basement Membrane (10 mg/ml, BD Biosciences, Bedford, Mass., USA): EBM-2 medium. After 45 minutes of polymerization at 37° C., EPDC were plated at $10^4$ cells/well in EBM supplemented or not with rh-sCD146 or VEGF. After 5 hours, pictures of representative fields were taken for each condition under an inverted microscope at 400× magnification. Capillary tube formation was evaluated by measuring the total tube length and the number of tubes per field with the Lucia® software (Nikon).

Cell Proliferation Assay

EPDC were seeded on 96-well plates ($5.10^3$/well) and cultured in EGM-2 medium for 3 days. Cells were then preincubated for 2 hours in EBM-2 medium. Cell proliferation was assayed by 5-bromo-2'-deoxy-uridine (BrdU) incorporation into cellular DNA using the BrdU Labeling and Detection Kit III from Roche Corporation. In brief, cells were incubated 12 hours with BrdU labeling solution in EBM-2 medium in the absence or presence of rh-sCD146 or VEGF. Cellular DNA was partially digested by nuclease treatment and incorporated BrdU was detected with peroxidase-conjugated primary antibodies. The absorbance was measured at 405 nm using a Uvmc2 micro-plate reader (Safas, Monaco). Results were expressed as arbitrary units. Experiments were performed in triplicates.

Wound Healing Assay

A reproducible wound was made with a pipet tip on a confluent monolayer of EPDC cultured on 24-well plates. The surface of the wound was measured at 400× magnification using an Olympus inverted microscope and acquired with the Biocom Visiolab image analysis software (Les Ulis, France). The medium was removed and EPDC were incubated for 6 hours with EBM-2 containing or not different concentrations of rh-sCD146. Cell wound repair was calculated by subtracting the wound area measured after 6 hours of incubation from the area of the original wound. Results were expressed as a percentage of the area of the original wound, considered as 100%.

Western-blot Analysis

Western-blot analysis was performed as followed. Briefly, cells were grown on plates treated or not with rh-sCD146, then washed in PBS, scraped off the plates and extracted with 300 µl of ice-cold lysis buffer (150 mM NaCl, 50 mM Tris HCl (pH 7.4), 2.4 mM EDTA, 1% Nonidet P40, 0.5 mM phenylmethylsulfonyl fluoride) for 30 min at 4° C. After centrifugation (12,000 g, 10 min, 4° C.) to eliminate cell debris and nuclei, proteins were quantified by protein assay (Biorad). 30 g of protein were resuspended in 40 µl of NuPage LDS sample Buffer (Invitrogen). Samples were then submitted to 4-12% NuPage SDS-polyacrylamide gel electrophoresis (Invitrogen) and transferred onto nitrocellulose membrane (Invitrogen). Membranes were probed with specific primary antibodies (anti-KDR, anti uPa, anti-MMP-2, anti e-NOS (see below)) followed by secondary antibodies coupled to peroxidase and revealed with the ECL kit (Amersham). Membranes we probed with various antibodies after stripping.

Gene Expression Profiling

Total cellular RNA was isolated from cultured EPDC treated or not for 3 hours with 50 ng/ml rh-sCD146. This was performed using the RNeasy Kit (Qiagen GmbH, Hilden, Germany) according to the manufacturer's instructions including the DNase digestion step. Oligoarray hybridizations were performed according to the manufacturer using angiogenesis oligoarrays (Tebu-Bio). Spots were quantified using the Tebu-Bio software. Subtraction of background was done for the signal mean intensities in both test and reference DNA spots. Normalization in the calculated ratios was done against the average of all ratios. The hybridizations were performed three times and data were taken from one representative experiment.

RNA Isolation, cDNA Synthesis and Real Time PCR

Total cellular RNA was isolated from EPDC using the RNeasy Kit (Qiagen GmbH, Hilden, Germany) according to manufacturer's instructions including the DNase digestion step. 5 µg of total RNA were reverse transcribed in a 50 µl reaction containing 40 U RNaseOUT (Invitrogen, Frederick, Md., USA), 150 ng of random hexamer primers (Roche Manheim, Germany), 10 mM dNTPs (Invitrogen), and 200 U of Superscript II (Invitrogen). The cDNA sample (0.2 µl) was subjected to qPCR using primer sets specific for the various genes or control genes at an optimized oligonucleotide concentration of 0.4 µW. Forward (F) and reverse (R) specific primer sequences were:

```
UPA-F:    TTTGCGGCCATCTACAGGAG        (SEQ ID NO: 18)
UPA-R:    AGTTAAGCCTTGAGCGACCCA       (SEQ ID NO: 19)
KDR-F:    TGTGGGTTTGCCTAGTGTTTCT      (SEQ ID NO: 20)
KDR-R:    CACTCAGTCACCTCCACCCTT       (SEQ ID NO: 21)
eNOS-F:   CTCATGGGCACGGTGATG          (SEQ ID NO: 22)
eNOS-R:   ACCACGTCATACTCATCCATACAC    (SEQ ID NO: 23)
MMP2-F:   TGATCTTGACCAGAATACCATCGA    (SEQ ID NO: 24)
MMP2-R:   GGCTTGCGAGGGAAGAAGTT        (SEQ ID NO: 25)
```

Reactions were performed in a total volume of 20 µl using the FastStart DNA Master$^{Plus}$ SYBR Green I kit according to the manufacturer's instructions (Roche). Amplification cycles were as following: 10 min at 95° C. (hot start PCR), followed by 40 cycles of 10 sec at 95° C., 10 sec at 62° C. and 20 sec at 72° C. (product amplification). At the end of amplification cycles, melting temperature analysis was performed by slow increase in temperature (0.1° C./sec) up to 95° C. Amplification, data acquisition and analysis were performed using a Light Cycler instrument and the LightCycler 3.5.2 software (Roche). The threshold cycle (Ct) for each gene was normalized to that of GAPDH. The values given refer to the number of transcript copies for a given gene for $10^6$ GAPDH transcript copies.

Peptides, Antibodies and Inhibitors

A recombinant human soluble form of CD146 (rh-sCD146) and its FITC conjugated version were prepared. This peptide corresponds to an N-terminal c-myc epitope tagged extracellular domain of human CD146 (EQKLISEEDL (SEQ ID NO: 26)). The tag was used for specific tracking of the exogenous recombinant protein and for control immunodepletion experiments. The corresponding c-myc peptide (Abcam) was used as a control. Fc-CD146 was generated by fusing the Fc part of human IgG1 with the extracellular part of human CD146. Anti-KDR (Sigma), anti uPa (American diagnostic inc.), anti-MMP-2 (Calbiochem), anti e-NOS (Santa Cruz Biotechnology), anti-CD146 (clone S-Endo-1; Biocytex), anti-CD31 (B&D), anti CD45 (B&D), anti CD33 (B&D), and anti-CD117 (B&D) antibodies were used at 1/500 dilution. Anti-mouse antibodies used in this study are: anti-CD45, anti-CD34, anti-asma, anti-MOMA2 (Dako Inc.; Glostrup; Denmark), Alexa fluor 488 anti-CD31 and Alexa fluor 647 anti-CD117 (Biolegend), anti-CD33 (Santa Cruz) and anti-CD146.

Anti-rat antibodies used in this study are: anti-CD117 (Neuromics), and anti-CD146. An anti-VEGFR2 blocking antibody was used (r212; Acris Antibodies GmbH, Herford; Germany).

An immunoassay was used to determine VEGF concentration in culture medium. Experiments were performed as described by the manufacturer (Invitrogen).

Statistical Analysis

Data were expressed as mean±SEM of the indicated number of experiments. Statistical analysis was performed with the Prism software (GraphPad Software Inc., San Diego, USA). Significant differences were determined using non parametric Mann Whitney test. A P value <0.05 was considered as significant.

Results

Recombinant Human Soluble CD146 Displays Chemotactic Activity on Endothelial Cells in vivo and in vitro Inventors investigated the chemotactic properties of rh-sCD146 on endothelial cells by implanting in non immunocompromised mice a three-dimensional matrigel plug containing rh-sCD146 (0.1 µg/µl). The c-myc peptide (0.1 µg/µl) was used as a control molecule since rh-sCD146 is myc-tagged (see Materials and Methods). Results showed that, after 14 days, rh-sCD146 Matrigel plugs contained about 100 times more cells than the control Matrigel plugs. These cells were able to organize into vascular-like structures and most of them were positively stained for CD31, illustrating that they were from endothelial origin (FIG. 1A).

To examine the different cell types present in matrigel plugs filled with rh-sCD146, stainings were performed with CD31, CD45, CD34, α-SMA, CD117 and MOMA-2. Results presented in FIG. 1B show that hematopoietic cells (CD45 positive), monocytes/macrophages (MOMA-2 positive), smooth muscle cells and/or pericytes (α-SMA positive) and endothelial cells (CD31 positive) could be recruited by rh-sCD146. Among the cells integrated in vascular-like structures, inventors observed CD34 positive cells (a marker of hematopoietic stem cells and of progenitor/ mature endothelial cells) and immature cells stained by the undifferentiation marker CD117. To better characterize these cells, co-stainings were performed (FIG. 1B). Results show that CD31 positive cells implicated in vascular-like structures were also CD146 positive. Interestingly, about 10-15% of CD31 positive or CD146 positive cells present in vascular-like structures were co-stained with the undifferentiation marker CD117 (FIG. 1B). Finally, double labelling CD117+/CD33– and CD117+/CD45– showed that these undifferentiated cells were not of myeloid or hematopoietic origin.

Inventors performed the same type of matrigel plugs experiments in nude mice injected with human EPC (FIG. 1B). Matrigel plugs implanted in nude mice and containing rh-sCD146 (1 µg/µl) were able to mobilize a large number of cells compared to control plugs, as already observed in normal mice (see above). Part of these cells were human EPC, as demonstrated by the positive labelling with an anti-human CD31 antibody, whereas no human EPC was observed in control plugs in the same animals. Interestingly, EPC also participated in the elaboration of structured vessels (FIG. 1B).

The chemotactic activity of rh-sCD146 on EPC was confirmed in vitro (FIG. 1C). The chemotactic activity of rh-sCD146 was increased from 0 to 50 ng/ml and then remained in plateau up to 400 ng/ml. The chemotactic effect observed with 50 ng/ml rh-sCD146 was similar to that observed with 20 ng/ml VEGF. No chemotactic activity could be detected in samples treated with either the c-myc peptide or buffer solution after immunodepletion of rh-sCD146. Altogether, these results demonstrate that rh-sCD146 was able to mobilize both mature and immature endogenous endothelial cells and exogenously administrated EPC. This is an important property of the molecule since EPC constitute major actors in angiogenesis and vasculogenesis.

Figure 2A:
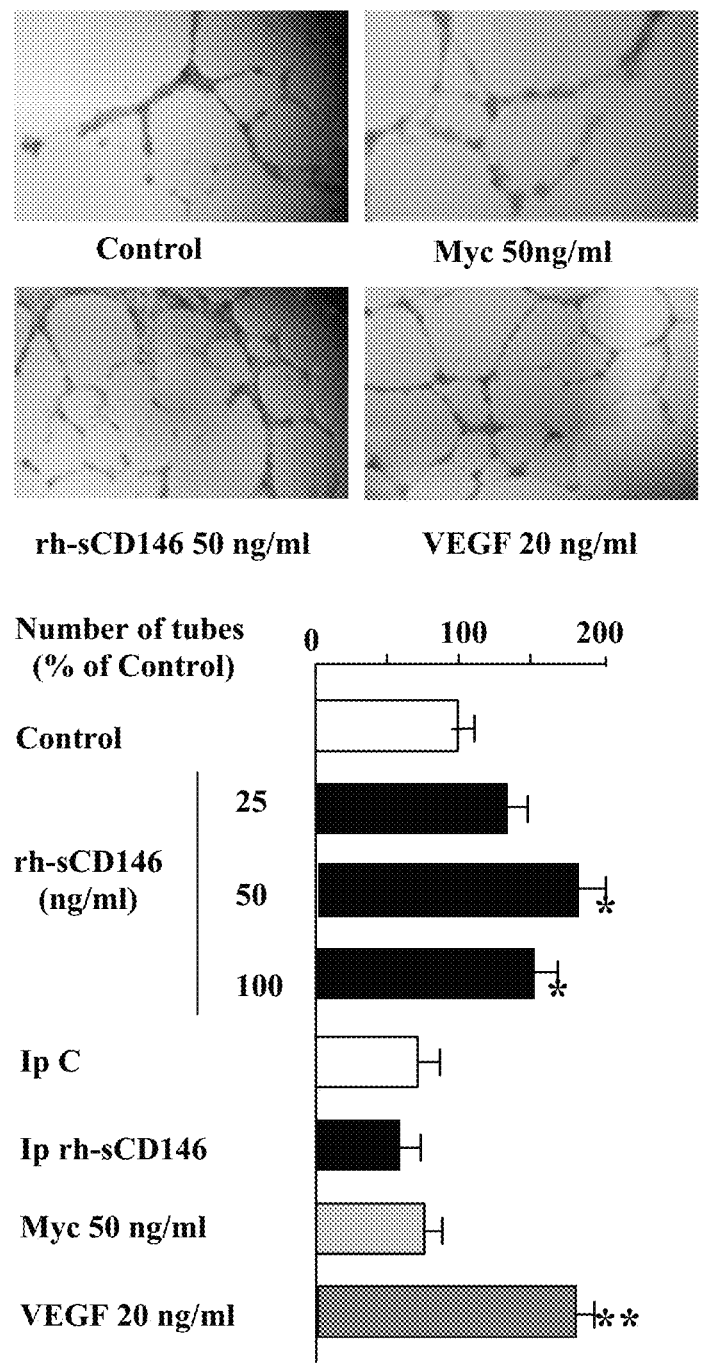

Recombinant Human Soluble CD146 Increases Angiogenic Capacity of Endothelial Progenitor Cells (EPC) in vitro Inventors examined the influence of rh-sCD146 on the functional properties of EPC. For this purpose, they evaluated the effects of different concentrations of rh-sCD146 on EPC tube formation, migration and proliferation and compared these effects with those of the angiogenic cytokine VEGF. The formation of capillary tubes was evaluated in a model of Matrigel plug, a laminin-based gel that mimics the cell microenvironment and enables tri-dimensional cell organization (FIG. 2A). When EPC were seeded on matrigel plugs, spontaneous formation of endothelial tubes occurred, the tubes forming in turn a capillary network. The addition of rh-sCD146 improved the development of this network as illustrated by the increase in tube number (FIG. 2A) and length (data not shown). This effect was dose-dependent between 25 and 100 ng/ml rh-sCD146. The effect observed with 50 ng/ml rh-sCD146 was similar to that observed with 20 ng/ml VEGF. No effect was observed when cells were treated with the control c-myc peptide or with immunodepleted rh-sCD146. The effect of rh-sCD146 was also evaluated on EPC proliferation (FIG. 2B) and migration (FIG. 2C). In both cases, the effect of rh-sCD146 was specific of the molecule (no effect of the buffer after immuno-depletion of rh-sCD 146) and dose-dependent. In these experiments, the effect of 50 ng/ml rh-sCD146 was also similar to that observed with 20 ng/ml VEGF.

Thus, in addition to recruiting EPC, rh-sCD146 appeared to be able to activate these cells by increasing their angiogenic activity. EPC proliferation, migration and capacity to organize into vascular-like structures in Matrigel plugs were increased at an extent very similar to that observed with VEGF.

Since the pioneering work of Folkman and colleagues in 1971, the therapeutic potential of several angiogenic growth factors has been extensively investigated.

Among them, VEGF has been repeatedly shown to increase angiogenesis and numerous therapeutic approaches have been tested based on the injection of either VEGF peptides or plasmid DNA encoding VEGF (Nomi M, Miyake H, Sugita Y, Fujisawa M, Soker S. Role of growth factors and endothelial cells in therapeutic angiogenesis and tissue engineering. Curr Stem Cell Res Ther. 2006; 1:333-43).

bFGF has also been shown to increase collateral arteriolar growth and experiments have suggested an interdependence between VEGF and bFGF (Stavri G T, Zachary I C, Baskerville Pa., Martin J F, Erusalimsky J D. Basic fibroblast growth factor upregulates the expression of vascular endothelial growth factor in vascular smooth muscle cells. Synergistic interaction with hypoxia. Circulation. 1995; 92 (1) :11-4).

Angiopoietin-1, which mediates the recruitment of vascular smooth muscle cells by developing vessels, erythropoietin (EPO) and granulocyte-colony stimulating factor (G-CSF) also appear to be involved in the collateral formation of vessels after ischemia in infarcted myocardium (Vandervelde S, van Luyn M J, Tio R A, Harmsen M C. Signaling factors in stem cell-mediated repair of infarcted myocardium. J Mol Cell Cardiol. 2005; 39(2):363-76). Finally, the endothelial nitric oxide synthase e-NOS was shown to display a potent angiogenic effect in ischemic tissues (Duda D G, Fukumura D, Jain R K., Role of eNOS in neovascularization: NO for endothelial progenitor cells. Trends Mol Med. 2004; 10:143-5).

The soluble form of CD 146 now appears as a new very relevant angiogenic growth factor, as herein demonstrated by inventors. Inventors' in vitro experiments indeed show that the effects obtained with 50 ng/ml rh-sCD146 were similar to that observed with 20 ng/ml VEGF (FIG. 2).

Figures 5A, 5B:
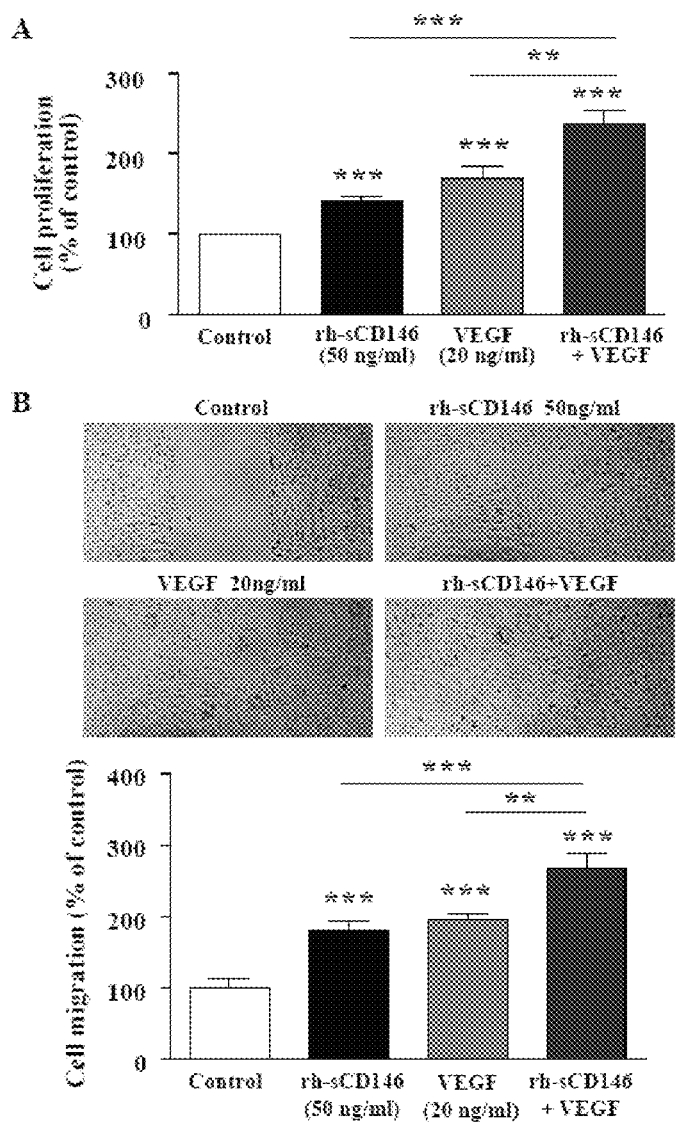
Figure 5C:
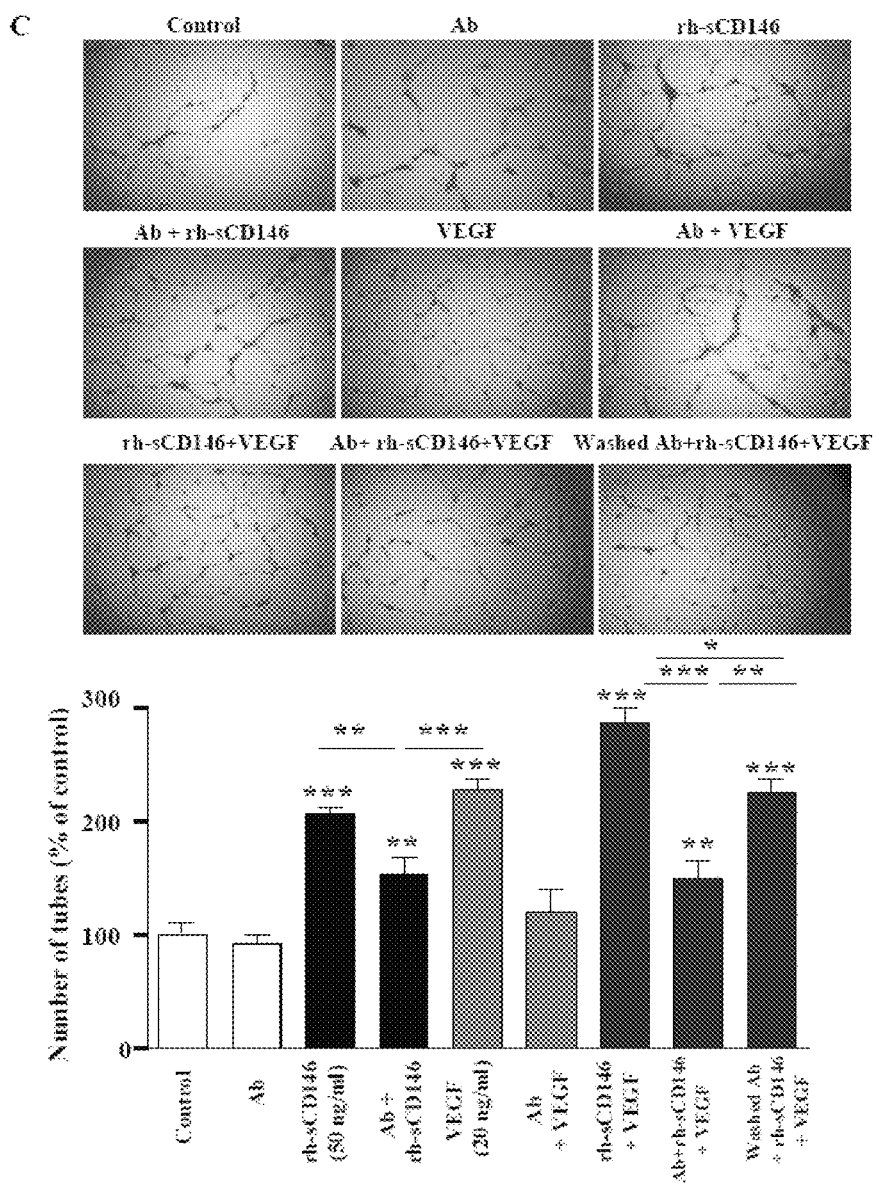

As rh-sCD146 and VEGF effects were very similar, inventors tested whether their effects were additive, synergistic or not. To this end, the same experiments were performed with the addition of both factors, rh-sCD146 50 ng/ml and VEGF 20 ng/ml (FIG. 5). Results show that effects of both molecules are additive on EPC proliferation (FIG. 5A), migration (FIG. 5B) and ability to form capillary-like structures in matrigel (FIG. 5C). To go further in the mechanism, they performed additional experiments of capillary tubes formation in matrigel in the presence of anti-VEGFR2 antibodies. These antibodies were either incubated with the cells all along the treatment with VEGF and/or rh-sCD146 to totally block VEGFR2, or preincubated with the cells before antibodies washing and further treatment with rh-sCD146 plus VEGF. This last condition allows blocking VEGFR2 present on the membrane before stimulation, but not VEGFR2 eventually induced by rh-sCD146.

Results (FIG. 5C) show that anti-VEGFR2 antibodies 1/had no effect in control condition, 2/totally blocked the VEGF effect, and 3/partially blocked the effect of rh-sCD146. When rh-sCD146 and VEGF were added in the presence of antibodies, the number of capillary-like structures was decreased as compared to the condition without antibodies, and the number of tubes was similar to that observed with rh-sCD146 in the presence of anti-VEGFR2 antibodies. Finally, when cells were pre-treated with the anti-VEGFR2 antibodies before washing of the antibodies and further stimulation with rh-sCD146 and VEGF, the number of capillary-like structures was significantly higher than in the previous condition, suggesting the induction of new VEGFR2 by rh-sCD146 at the cell surface. Altogether, these experiments indicate that rh-sCD146 response involves in majority a sCD146-specific pathway but also, in a minor part, the VEGF signalling pathway, by inducing new VEGFR2 at the cell surface.

Experiments were also performed to test whether VEGF secretion was modified by rh-sCD146 treatment. EPC treated for 24hours with 50 ng/ml rh-sCD146 exhibited a statistically significant increase in VEGF secretion as compared to non-treated EPC (71.8+/−6.1 versus 54.8+/−3.2 pg/ml, n=6; p<0.05).

Figure 3A:
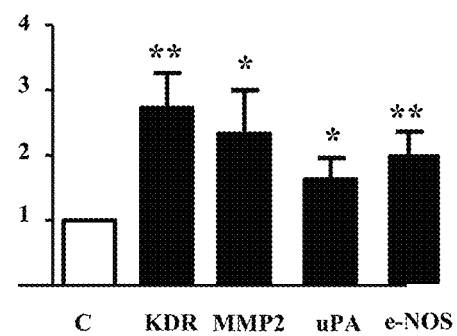
Figure 3B:
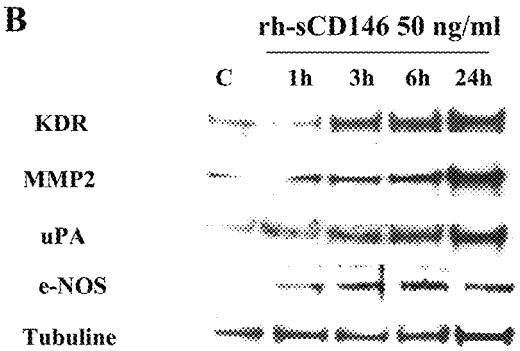
Figure 3C:
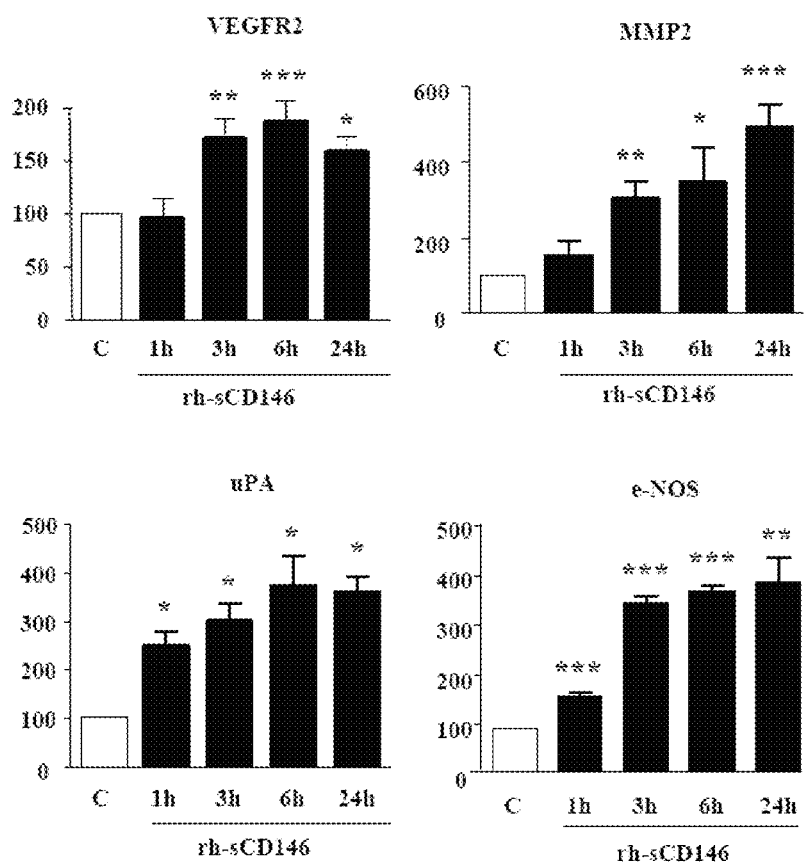

Recombinant Human CD146 Induces Transcription of Pro-angiogenic Genes in Endothelial Progenitor Cells Inventors hypothesized that the functional effects of rh-sCD146 observed on EPC could depend in part on gene transcription. To test this hypothesis, they monitored alterations in gene expression upon treatment of EPC with rh-sCD146 using oligo-arrays specific for angiogenic genes. Among the 113 probed genes (see Methods), some were up-regulated, others were down-regulated or not modified. Among the up-regulated genes, they choose four genes that were reproducibly up-regulated at least 5-fold in EPC treated for 3h with 50 ng/ml rh-sCD146. They included eNOS, the VEGF receptor 2 (KDR), the matrix metallopeptidase MMP-2 and the plasminogen activator urokinase (PLAU/u-Pa) (FIG. 3). Alterations in expression of these genes upon treatment of EPC with 50 ng/ml rh-sCD146 were confirmed by qPCR and Western-blot analysis. qPCR experiments revealed that mRNAs for all four genes were effectively significantly increased 3 hours after treatment with 50 ng/ml rh-sCD146 (FIG. 3A). At the protein level, expression of eNOS and u-Pa increased significantly 1 h after treatment while the increase in KDR and MMP-2 was observed 3 h post-treatment (FIGS. 3B and 3C). Increased protein expression was sustained for 24 hours.

Thus, one of the main effects of rh-sCD146 was to increase the transcription and translation of several pro-angiogenic proteins. Proteins that are up-regulated by rh-sCD146 in this study appear to be of particular importance during angiogenesis.

The activity of KDR in particular is dramatically increased during vasculogenesis or during tumor angiogenesis. It acts on endothelial cells by inducing the expression of several proteins such as uPA, uPAR and some MMPs. Two other proteins induced by rh-sCD146 in our study are u-PA and MMP-2. They belong to proteolytic complexes which promote the degradation of the basal membrane and of the extracellular matrix during migration and cellular proliferation. They are involved both in physiological and tumoral angiogenesis. Of interest, the activity of CD146 often appears to be coupled to that of MMP-2. Indeed, it has been shown that the treatment of melanoma by anti-MUC18 antibodies decreased the capacity of HUVEC to colonize Matrigel plugs in vitro and that this was associated with a decrease in the collagenase activity of MMP-2.

eNOS, another rh-sCD146-induced protein, also appears to play a key role in angiogenesis. The role of eNOS in the mobilization of stem cells appears to be essential. Pretreatment of bone marrow mononuclear cells derived from patients with ischemic cardiomyopathy with the eNOS synthase transcription enhancer AVE9488 is able to restore the capacity of these progenitor cells to induce neovascularisation.

Figure 4A:
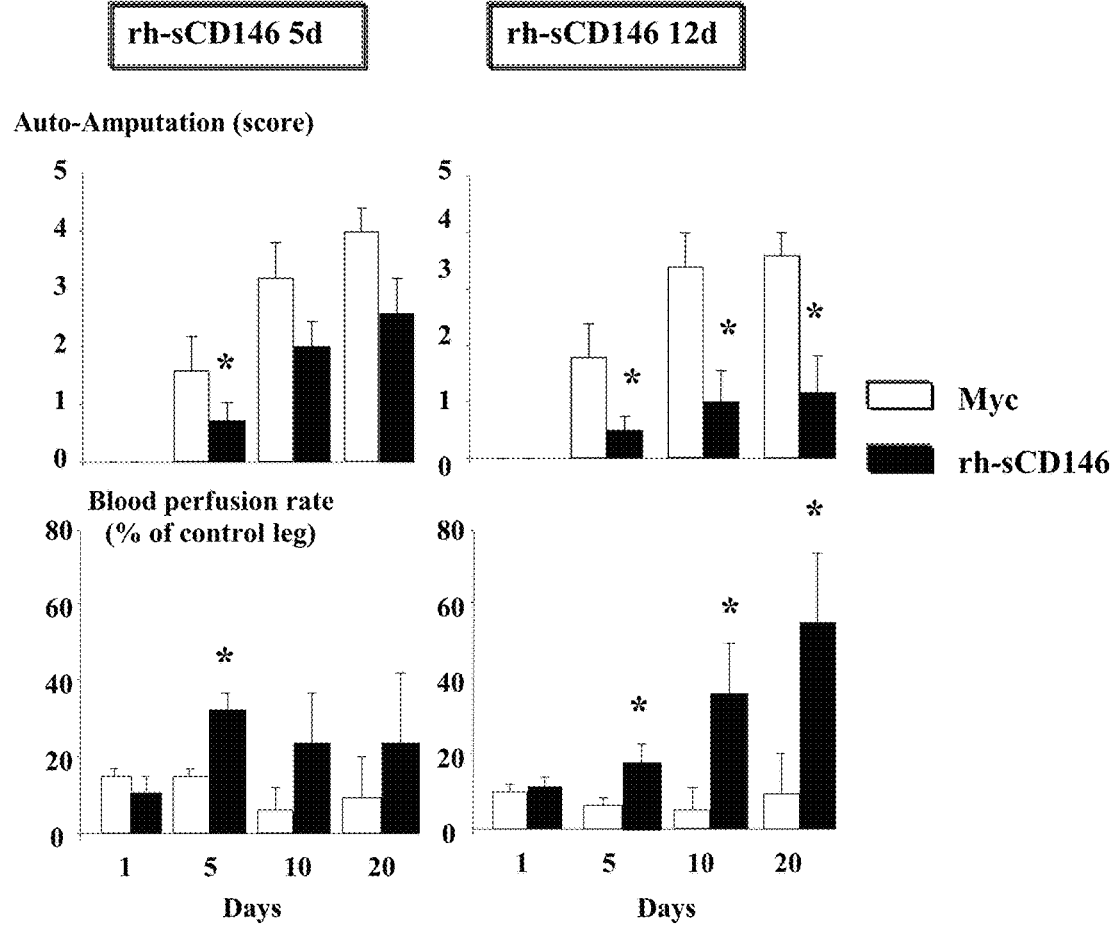
Figure 4B:
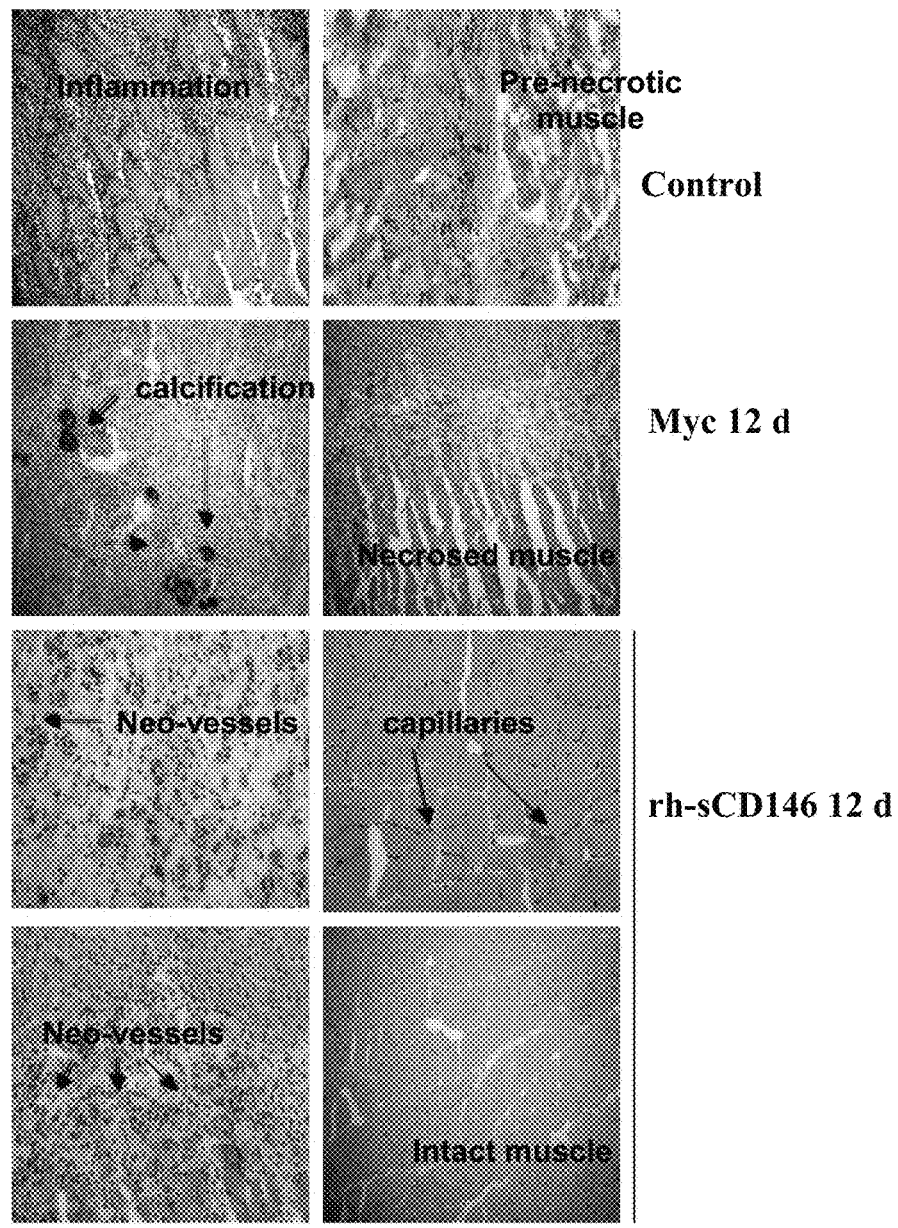

Local Injection of Recombinant Human Soluble CD146 Increases Neovascularisation in a Rat Ischemic Hind Limb Model In light of the in vitro and in vivo properties of rh-sCD146, inventors tested its potential therapeutic effects in an in vivo model of rat hindlimb ischemia. Results presented in FIG. 4A showed that, after 5 days of treatment of the ischemic hindlimb with 10 µg rh-sCD146/day, the level of auto-amputation of the animals was significantly decreased 5 days after initiation of ischemia, as compared to control animals treated with the c-myc peptide. In contrast, it was not significantly different between treatment groups 10 or 20 days post initiation of ischemia. Laser-doppler tissue imaging showed that obstruction of the left common femoral artery decreased blood perfusion by about 90% at day 1. Treatment with rh-sCD146 significantly increased the blood perfusion rate at day 5 as compared to the control group but no further significant modification in blood flow was detectable between the two groups at days 10 and 20. When animals were treated with the same dose of rh-sCD146 (10 µg/day), but for a longer period of time (12 days), the auto-amputation level was now significantly decreased at day 5, 10 and 20, as compared to control rats. In these conditions, the blood perfusion rate was also significantly increased from day 5 to day 20, reaching about 60% of the blood perfusion rate in the control leg of the same animals at day 20 (FIG. 4A). Histochemical examination of muscle sections after 20 days showed inflammation, calcification, fibrosis areas and numerous necrosed muscular fibers in ischemic hindlimbs that were not treated by rh-sCD146 (FIG. 4B). In contrast, in ischemic hindlimbs treated with rh-sCD 146 for 12 days, almost no fibrosis was observed, inflammation and necrosed muscular fibers were highly reduced (FIG. 4B and FIG. 4C). Examination of capillaries showed that their number was significantly increased, as compared to control ischemic limbs, and muscle aspect was greatly improved with a majority of intact muscular fibers (FIG. 4B and FIG. 4C). Interestingly and advantageously, inventors also observed a trophic effect of rh-sCD146 on healing of amputated limbs (data not shown).

Figure 4D:
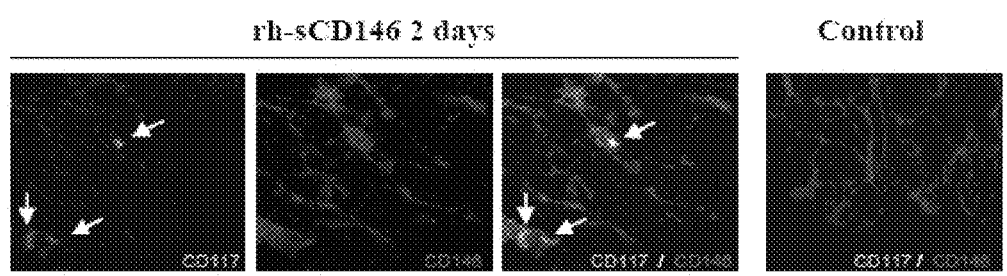

As CD117/CD146 positive endothelial precursor cells participating in vascular-like structures were observed in vivo in matrigel plugs containing rh-sCD146 (see FIG. 1B), inventors tested whether such cells could also be detected in rat muscles after ischemia. To this end, inventors analyzed muscles of rats with hind limb ischemia, treated or not with rh-sCD146, two days after the beginning of the treatment in order to detect early events. Results show that CD117/CD146 positive cells could be detected in rh-sCD146 treated animals whereas these cells were not found in control rats (FIG. 4D).

CONCLUSION

Experiments of matrigel plugs in vivo showed that sCD146 displayed chemotactic activity on different cell types, including endothelial cells, as attested by their insertion into vascular-like structures and their positive staining for endothelial marker as CD34, CD146 or CD31 (double staining of these cells show that they are CD33 and CD45 negative, indicating that they are not of myeloid or hematopoietic origin), and hematopoietic cells such as monocytes, smooth muscle cells and/or pericytes. These experiments further showed that sCD146 was able to recruit exogenously injected late endothelial progenitor cells (EPC), also herein identified as EPDC.

Recruited endothelial cells participated in formation of vascular-like structures. In vitro, sCD146 enhanced angiogenic properties of EPC, with an increased cell migration, proliferation and capacity to establish capillary-like structures.

Up to now, the receptor of soluble CD146 is still unknown. The membrane CD146 is not this receptor since no homophilic interactions between both molecules has been evidenced.

Observed effects were, in particular, additive with those of VEGF. sCD146 enhanced VEGFR2 expression and VEGF secretion.

Consistent with a pro-angiogenic role, gene expression profiling of sCD146-stimulated EPC revealed, in particular, an up-regulation of eNOS, uPa, MMP2 and VEGFR2. Silencing membrane-bound CD146 inhibited these responses.

The potential therapeutic interest of sCD146 was tested in a model of hindlimb ischemia. The present invention demonstrates that local injections of sCD146 significantly reduced auto-amputation, tissue necrosis, fibrosis, inflammation, and increased blood flow. It is herein established that sCD146 displays chemotactic and angiogenic properties and promotes efficient neovascularisation in a model of limb ischemia. Recombinant human sCD146 thus support novel strategies for therapeutic angiogenesis in ischemic diseases and disorders.

The complete mechanism governing the favourable effects of sCD146 is unknown and remains to be established but several pathways could be involved. sCD146 could act on local endothelial resident cells and/or monocyte infiltration since inventors evidenced a chemotactic effect on monocytes in matrigel plugs in vivo (Bardin N, Blot-Chabaud M, Despoix N, et al. CD146 and its soluble form regulate monocyte transendothelial migration. Arterioscler. Thromb Vasc Biol. 2009; 29: 746-53). Alternatively, or additionally, sCD146 may play a role in vasculogenesis by recruiting endothelial progenitor cells to area of neovascularisation. In agreement with this last hypothesis, cells presenting characteristics of late endothelial progenitors were recruited in matrigel plugs and organized as vascular-like structures. In addition, immature endothelial cells could be observed in muscle sections of animals after two days of treatment with sCD146.

Example 2

Study of the Healing Activity of an Active Principle on the Cutaneous Healing Kinetics on Living Human Skin Explants The aim of the study was to demonstrate the activity of sCD146 on the healing kinetics of epidermal and dermal lesions induced by UVB irradiation on living skin explants. This activity was evaluated by observation of the general morphology, and by specific immunolabels for fibronectin and integrin β4.

Operating Method

Preparation of the Explants

Thirty explants from an abdominoplasty of a 42-year old woman (P718AB42) were prepared and kept alive in BIO-EC's Explant Medium (BEM).

The explants were divided into 2 lots of 9 explants and 2 lots of 6 explants in a 12-well culture dish each containing 1 mL BEM as follows:

| Lot | Nature | Number of explants |
|---|---|---|
| N | Normal untreated skin | 9 |
| B | Burned untreated skin | 9 |
| BP1 | Burned skin + P1 (topical application) | 6 |
| BP2 | Burned skin + P2 (incorporated in the culture medium) | 6 |

Epidermal and Dermal Lesions

Epidermal and dermal lesions were created by UVB irradiation of 10 $J/cm^2$, delivered by a Vilber Lourmat UV simulator with a RMX3W control unit. The burning was limited to the center of the explant over a 4 mm diameter area.

2. Application of the Products sCD146 was tested at a concentration of 7.5 μg per explant. It was applied topically (30 μL on a filter paper disk applied onto the explant) (P1) and 19 μL incorporated in 1 mL BEM (P2). The P1 and P2 products were applied topically and incorporated into the BEM on D0, D2, D5, D6 and D8. The culture media were refreshed at the same time.

3. Samples

On D0, the 3 explants of lot N and B were sampled at the end of irradiation. They were cut in half: one half was fixed in ordinary Bouin's solution and the other half was stored at −80° C. At time D4 and D11, 3 explants from each lot were sampled and treated in the same way.

4. Histology

After 48 hours of fixation in the Bouin's solution, the samples were dehydrated and impregnated in paraffin by means of a Leica 1020 tissue processor. They were embedded according to operating procedure MO-H-153 by means of a Leica EG 1160 embedding center. Sections of 5 μm were made according to operating procedure MO-H-173 by means of a Leica RM 2125 Minot mictrotome and affixed to Superfrost® histologically-silanized glass slides. Frozen samples were sectioned at 7 μm in a Leica CM3050 cryostat. The sections were affixed onto histologically-silanized glass slides for the immunological labeling. The microscopic observations were made by light microscopy, by means of a Leica Orthoplan microscope, with a X25 objective. The photographs were taken with a Sony DXC 390P tri CCD camera and stored by Leica 1M1000 data archiving software.

4.1 General Morphology

The general morphology was observed on paraffin sections after staining with Masson's trichrome, Goldner's variant, according to operating procedure MO-H-157.

4.2 Fibronectin Immunolabeling

Fibronectin was labelled on frozen sections, with a mouse anti-fibronectin monoclonal antibody, clone TV-1, from Chemicon (ref MAB 88904), at $1/50^{th}$ for 1 h at ambient temperature with a biotin/streptavidin amplifier system, revealed by FITC, with the nuclei counterstained with propidium iodide. This labeling was done on the explants sampled at T0 and D4.

4.3 Immunolabeling of Integrin β4

Integrin β4 was labeled on frozen sections with a mouse anti-integrin β4 monoclonal antibody, clone 3E1 from Chemicon (ref MAB 1964), at $1/600^{th}$ for 1 hour 30 minutes at ambient temperature, with a biotin/streptavidin amplifier system, revealed by FITC, with the nuclei counterstained with propidium iodide. This labeling was done on the explants taken at T0 and D11.

Activity Criteria Examined

The healing activity was examined on the edges and on the lesion induced by UVB.

Glossary of Histological Terms Used:

Spongiosis: intercellular oedema without breaking the desmosomal bonds.

Acantholysis: intercellular oedema with breaking of the desmosomal bonds.

Pycnotic nuclei: nuclear degeneration leading to cell necrosis.

Cellular oedema: swelling of the cell

Epidermal acanthosis: increase in the thickness of the epidermis due to an increase in the number of cell layers or an increase in the size of the keratinocytes.

Parakeratosis: keratinization of the stratum granulosum, the last living epidermal layer.

Results

General Morphology

On D0:

Unburned Lot (N0)

The stratum corneum is thick, moderately lamellar, moderately keratinized on the surface and at its base. The epidermis has 4 to 5 cell layers with good morphology. The dermal-epidermal junction topography is moderate. The papillary dermis has fairly thick collagen fibres forming a fairly dense network. It is well cellularized.

Burned Lot (B0)

The stratum corneum is thick, fairly lamellar, moderately keratinized on the surface and at its base. The epidermis has 4 to 5 cell layers with good morphology. The dermal-epidermal junction topography is moderate. The papillary dermis has fairly thick collagen fibres forming a fairly dense network. It is well cellularized.

On D4:

Unburned Lot (NJ4)

The stratum corneum is thick, slightly lamellar, slightly keratinized on the surface and at its base. The epidermis has 4 to 5 cell layers with good morphology. The dermal-epidermal junction topography is moderate. The papillary dermis has fairly thick collagen fibres forming a fairly dense network. It is well cellularized.

Untreated Burned Lot (BJ4)

On the unburned zone, the stratum corneum is thick, moderately lamellar, slightly keratinized on the surface and at its base. The epidermis has 4 to 5 cell layers with good morphology. The dermal-epidermal junction topography is moderate. The papillary dermis has fairly thick collagen fibres forming a fairly dense network. It is well cellularized.

On the lesion, the alterations are very marked, with rather numerous keratinocytes with clearly pycnotic nuclei and perinuclear oedema. The keratinocytes have good morphology and are present in moderate numbers, primarily basally.

On the edges of the lesion, the keratinocytes have good morphology, have a fairly strong presence and are moderately stratified. The keratinocyte growth bud is moderate, somewhat thick, with a moderate progression of neo-keratinocytes under the altered structures.

Burned+product P1 Lot (BP1J4)

On the unburned zone, the stratum corneum is thick, slightly lamellar, moderately keratinized on the surface and at its base. The epidermis has 4 to 5 cell layers with good morphology. The dermal-epidermal junction topography is fairly marked. The papillary dermis has fairly thick collagen fibres forming a fairly dense network. It is well cellularized.

On the lesion, the alterations are marked, with fairly numerous, moderately oedematous keratinocytes with pycnotic nuclei and perinuclear oedema. The keratinocytes with a good morphology are moderate in number, primarily basally.

On the edges of the lesion, the keratinocytes have good morphology and are moderate in number, fairly regular and not very stratified. The keratinocyte growth bud is small and thin, with a poor progression of neo-keratinocytes under the altered structures.

Burned+Product P2 Lot (BP2J4)

On the unburned zone, the stratum corneum is thick, slightly lamellar, moderately keratinized on the surface with slight parakeratosis. The epidermis has 4 to 5 cell layers with good morphology. The dermal-epidermal junction topography is moderate. The papillary dermis has fairly thick collagen fibres forming a network that is not very dense. It is well cellularized.

On the lesion, the alterations are fairly moderate, with a moderate number of keratinocytes with pycnotic nuclei and perinuclear oedema. Keratinocytes with good morphology are fairly numerous basally and suprabasally with a few slightly stratified neo-keratinocyte zones.

On the edges of the lesion, keratinocytes with good morphology are clearly present and not very stratified. The keratinocyte growth bud is small and thin, with a poor progression of neo-keratinocytes under the altered structures.

On D11:

Unburned Lot (NJ11)

The stratum corneum is very thick, slightly lamellar, slightly keratinized on the surface, with very marked parakeratosis. The epidermis has 5 to 6 cell layers with moderately altered morphology. There is marked basal spongiosis. The dermal-epidermal junction topography is moderate. The papillary dermis has fairly thick collagen fibres forming a fairly dense network. It is well cellularized.

Burned and Untreated Lot (BJ11)

On the unburned zone, the stratum corneum is thick, moderately lamellar, moderately keratinized on the surface with advanced parakeratosis. The epidermis has 4 to 5 cell layers with a moderately altered morphology. There is marked basal spongiosis. The DEJ topography is moderate. The papillary dermis has somewhat thick collagen fibres forming a fairly dense network. It is well cellularized.

On the lesion, the alterations are very marked, with numerous keratinocytes with clearly pycnotic nuclei and perinuclear oedema. Keratinocytes with good morphology are scarce basally and non-stratified.

On the edges of the lesion, keratinocytes with good morphology are clearly present and fairly well stratified in 2 or 3 cell layers. The keratinocyte growth bud is very clear, moderately thick with a very marked progression of neo-keratinocytes under the altered structures (approximately 2.5 microscopic fields).

Burned+Product P1 Lot (BP1J11)

On the unburned zone, the stratum corneum is thick, moderately lamellar, slightly keratinized on the surface with very marked parakeratosis. The epidermis has 3 to 4 cell layers with moderately altered morphology. These alterations are characterized by the presence of a moderate number of moderately oedematous cells with pycnotic nuclei and perinuclear oedema in the upper epidermal layers. There is moderate basal spongiosis. The dermal-epidermal junction topography is moderate. The papillary dermis has fairly thick collagen fibres forming a network that is not very dense. It is well cellularized.

On the lesion, the alterations are marked, with very numerous keratinocytes with pycnotic nuclei and perinuclear oedema. Keratinocytes with good morphology are very scarce.

On the edges of the lesion, keratinocytes with good morphology are scarce, very irregular and not well-stratified. The keratinocyte growth bud is small and thin, poorly structured, with a poor progression of neo-keratinocytes under the altered structures.

Burned+Product P2 Lot (BP2J4)

On the unburned zone, the stratum corneum is thick, moderately lamellar, slightly keratinized on the surface, with very marked parakeratosis. The epidermis has 3 to 4 cell layers with clearly altered morphology. These alterations are characterized by the presence of numerous, clearly oedematous cells with pycnotic nuclei and perinuclear oedema in the upper cell layers. There is marked basal and suprabasal spongiosis. The dermal-epidermal junction topography is moderate. The papillary dermis has fairly thick collagen fibres forming a network that is not very dense. It is well cellularized.

On the lesion, the alterations are very marked, with numerous keratinocytes with pycnotic nuclei and perinuclear oedema. Neo-keratinocytes with good morphology are moderate in number basally, and slightly stratified.

On the edges of the lesion, keratinocytes with good morphology are clearly present and fairly well stratified. The keratinocyte growth bud is fairly clear and thin, slightly stratified over 2 to 3 cell layers, with a clear progression of neo-keratinocytes under the altered structures (approximately 2 microscope fields).

Fibronectin

No labeling is observed after replacing the primary antibody or secondary antibody by PBS, which shows the specificity of the labeling observed.

On D0:
Unburned Lot (N0)
The labeling is clear throughout the papillary dermis. It is dense and clearly filamentous.
Burned Lot (B0)
The labeling is clear throughout the papillary dermis. It is dense and clearly filamentous.

On D4:
Unburned Lot (NJ)
The labeling is fairly clear throughout the papillary dermis. It is dense and moderately filamentous.
Burned and Untreated Lot (BJ4)
On the unburned zone, the labeling is fairly clear throughout the papillary dermis. It is dense and moderately filamentous.
On the lesion, the labeling is fairly clear throughout the papillary dermis. It is fairly dense and clearly filamentous.
Burned+Product P1 Lot (BP1J4)
On the unburned zone, the labeling is fairly clear throughout the papillary dermis. It is dense and moderately filamentous.
On the lesion, the labeling is clear throughout the papillary dermis. It is dense and very clearly filamentous.
Burned+Product P2 lot (BP2J4)
On the unburned zone, the labeling is fairly clear throughout the papillary dermis. It is dense and moderately filamentous.
On the lesion, the labeling is clear throughout the papillary dermis. It is fairly dense and clearly filamentous.

Integrin β4

No labeling was observed after replacing the primary or secondary antibody by PBS, which shows the specificity of the labeling observed.

On D0:
Unburned Lot (N0)
The labeling is clear and regular. It is moderate laterally on the basal keratinocytes.
Burned Lot (B0)
The labeling is clear and regular. It is moderate laterally on the basal keratinocytes.

On D11:
Unburned Lot (NJ11):
The labeling is fairly clear and fairly regular. It is moderate laterally on the basal keratinocytes.
Burned and Untreated lot (BJ11):
On the unburned zone, the labeling is fairly clear and fairly regular. It is moderate laterally on the basal keratinocytes.
On the lesion, the labeling is moderate and irregular. It is very moderate laterally on the basal keratinocytes.
Burned+Product P1 Lot (BP1J11):
On the unburned zone, the labeling is fairly clear and regular. It is moderate laterally on the basal keratinocytes.
On the lesion, the labeling is fairly clear and fairly regular. It is very moderate laterally on the basal keratinocytes.
Burned+Product P2 Lot (BP2J11):
On the unburned zone, the labeling is fairly clear and fairly regular. It is moderate laterally on the basal keratinocytes.
On the lesion, the labeling is very clear and fairly regular. It is moderate laterally on the basal keratinocytes.

Discussion

General Morphology

| | On D 4 | | On D 11 | |
| --- | --- | --- | --- | --- |
| Lot | Neo-keratinocytes on the lesion | Intensity of the growth bud | Neo-keratinocytes on the lesion | Intensity of the growth bud |
| B | − | ++ | − | ++++ |
| BP1 | − | + | − | + |
| BP2 | + | + | ++ | +++ |

Neo-keratinocytes:
No neo-keratinocytes: −
Few neo-keratinocytes: +
Moderate number of neo-keratinocytes: ++
Numerous neo-keratinocytes: +++
Intensity of the growth bud:
Negative: −
Low: +
Moderate: ++
Marked: +++
Very marked: ++++

On D4:

Compared to the Burned and Untreated Lot:

Treatment with product sCD146 applied topically (P1) did not induce any epidermal restructuring activity either on the edges of the lesion or on the lesion itself. Treatment with sCD146 incorporated into the BEM (P2) induces a weak epidermal restructuring activity with the presence of a few basal neo-keratinocytes on the lesion.

At this time, mild epidermal intolerance reactions appeared, stronger on the lot treated with sCD146 applied topically.

On D11:

Compared with the Burned and Untreated Lot:

Treatment with sCD146 applied topically (P1) does not induce epidermal restructuring activity either on the edges of the lesion or on the lesion itself.

Treatment with sCD146 incorporated into the BEM (P2) induces a weak epidermal restructuring activity, characterized by the presence on the lesion of a moderate number of neo-keratinocytes and by the presence on the edges of a fairly marked epidermal growth bud.

At this time, marked epidermal intolerance reactions appear, very strong in the lot treated with CD146 applied topically and more moderate with product CD146 incorporated into the BEM.

Fibronectin

| | On D 4 | |
|---|---|---|
| Lot | Unburned | Lesion |
| B | ++ | +++ |
| BP1 | ++ | ++++ |
| BP2 | ++ | +++ |

Expression of fibronectin:
Negative: −
Low: +
Moderate: ++
Marked: +++
Very marked: ++++

On D0:

The fibronectin is clear in the papillary dermis. It is dense and clearly filamentous.

On D4:

On the unburned zones, the expression of fibronectin does not change.

On the injured areas, with sCD146 applied topically (P1), the overexpression of fibronectin is marked, showing a clearly more filamentous network, promoting the migration of fibroblasts of the papillary dermis. This overexpression is lesser with sCD146 incorporated into the survival medium (P2).

Integrin β4:

| | On D 11 | |
|---|---|---|
| Lot | Unburned | Lesion |
| B | +++ | ++ |
| BP1 | +++ | +++ |
| BP2 | +++ | ++++ |

Expression of integrin β4:
Negative: −
Low: +
Moderate: ++
Marked: +++
Very marked: ++++

On D0:

The expression of integrin β4 is clear and regular. It is moderate laterally on the basal keratinocytes.

On D11:

On the unburned and untreated lot, the expression of integrin β4 is fairly clear and fairly regular. It is moderate laterally on the basal keratinocytes.

On the Treated Lots

On the unburned zones, the expression of integrin β4 does not change much, regardless of the treatment, with regard to the untreated control.

On the injured zones, with sCD146 applied topically (P1); integrin β4 is moderately overexpressed with regard to the untreated control. It is clearly overexpressed with sCD146 incorporated into the survival medium.

CONCLUSION

General Morphology:

sCD146 incorporated into the BEM survival medium for 11 days induces the most marked epidermal restructuring activity observed, both on the edges of the lesion and on the lesion itself, characterized by the presence of a moderate number of slightly stratified neo-keratinocytes in the basal position. However, this activity is attenuated by rather marked epidermal intolerance reactions.

Fibronectin:

Fibronectin is an early dermal healing marker. Its overexpression, after 4 days of survival, indicates an improvement in its network in the papillary dermis, promoting the migration of fibroblasts, which will ultimately colonize the altered zone.

On the burned and untreated lot, the expression of fibronectin is increased on the lesion, which is a normal activity of dermal healing. The most marked overexpression of fibronectin is observed with sCD146 applied topically.

Integrin β4:

Integrin β4 is involved in anchoring keratinocytes onto the basement membrane at the hemidesmosomes. Its restructuring or maintenance is a favourable index for showing epidermal healing activity. sCD146 incorporated into the medium for 11 days induces the clearest activity on integrin β4.

The Above Detailed Experiments Demonstrate That:

sCD146 incorporated into the survival medium has the best activity with regard to keratinocyte stimulation and integrin β4 expression (as confirmed by data appearing on FIG. 8).

sCD146 applied topically has the best activity on dermal restructuring.

The invention claimed is:

1. A composition comprising human soluble CD146 protein consisting of SEQ ID NO: 7, wherein said human soluble CD146 protein is acetylated, methylated, phosphorylated or fused to another polypeptide and a pharmaceutically acceptable carrier.

2. The composition according to claim 1, further comprising an angiogenic factor selected from the group consisting of vascular endothelial growth factor (VEGF), stromal-cell-derived-factor-1 (SDF-1), basic fibroblast growth factors (bFGF), erythropoietin (EPO), granulocyte colony-stimulating factor (G-CSF), granulocyte-macrophage colony stimulating factor (GM-CSF), stem cell factor (SCF), interleukin-8 (IL-8) and mixtures thereof.

3. The composition according to claim 1, further comprising an endothelial progenitor cell (EPC), said cell having, optionally, been contacted with said human soluble CD146 protein.

4. A method of treating limb ischemia in a mammal comprising administering to the mammal an isolated human soluble CD146 protein consisting of SEQ ID NO: 7, said human soluble CD146 protein being optionally acetylated, methylated, phosphorylated, glycosylated or fused to another polypeptide, or a composition comprising said soluble CD146 protein and a pharmaceutically acceptable carrier.

5. An isolated human soluble CD146 protein consisting of SEQ ID NO: 7, wherein said human soluble CD146 protein is acetylated, methylated, phosphorylated or fused to another polypeptide.

6. The isolated human soluble CD146 protein of claim 5, wherein said human soluble CD146 protein is acetylated.

7. The isolated human soluble CD146 protein of claim 5, wherein said human soluble CD146 protein is fused to another polypeptide.

8. The isolated human soluble CD146 protein of claim 5, wherein said human soluble CD146 protein is methylated.

9. The isolated human soluble CD146 protein of claim 5, wherein said human soluble CD146 protein is phosphorylated.

* * * * *

UNITED STATES PATENT AND TRADEMARK OFFICE
CERTIFICATE OF CORRECTION

PATENT NO. : 9,605,048 B2  
APPLICATION NO. : 13/146758  
DATED : March 28, 2017  
INVENTOR(S) : Marcel Blot-Chabaud et al.

Page 1 of 1

It is certified that error appears in the above-identified patent and that said Letters Patent is hereby corrected as shown below:

In the Specification

Column 6,
Line 34, "either 1 μg/R1" should read --either 1 μg/μl--.

Column 31,
Line 33, "(CDT)," should read --(CDI),--.

Column 32,
Line 59, "(Abeam)" should read --(Abcam)--.

Column 32,
Line 65, "animal" should read --animal.--.

Column 35,
Line 42, "0.4 μW." should read --0.4 μM.--.

Column 36,
Line 22, "anti-asma," should read --anti-αsma--.

Signed and Sealed this
Twentieth Day of February, 2018

Andrei Iancu
*Director of the United States Patent and Trademark Office*